United States Patent [19]

Iwami et al.

[11] Patent Number: 5,192,678
[45] Date of Patent: Mar. 9, 1993

[54] CEPHALOSPORIN C ACYLASE

[75] Inventors: Morita Iwami, Tsukuba; Ichiro Aramori, Kyoto; Masao Fukagawa, Tsuchiura; Takao Isogai, Ibaraki; Hitoshi Kojo, Tsuchiura, all of Japan

[73] Assignee: Fujisawa Pharmaceutical Co., Ltd., Osaka, Japan

[21] Appl. No.: 747,901

[22] Filed: Aug. 20, 1991

[30] Foreign Application Priority Data

Sep. 10, 1990 [GB] United Kingdom ................. 9019724

[51] Int. Cl.⁵ .............................................. C12N 9/80
[52] U.S. Cl. ................................... 435/228; 435/69.1; 435/51; 435/172.3; 435/252.3; 435/252.33; 435/320.1; 935/14; 935/29; 935/56; 935/73; 536/23.2
[58] Field of Search ............ 435/228, 69.1, 51, 172.3, 435/252.3, 252.33, 320.1; 935/14, 29, 56, 73; 536/27

[56] References Cited

PUBLICATIONS

Matsuda, A. et al "Cloning and Characterization of the Genes for two Distinct Cephalosporin Acylases from a Pseudomonas Strain" J. Bacteriology vol. 169(12)5815–5820 (Dec. 1987).

*Primary Examiner*—Robert A. Wax
*Assistant Examiner*—Rebecca Prouty
*Attorney, Agent, or Firm*—Oblon, Spivak, McClelland, Maier & Neustadt

[57] ABSTRACT

A cephalosporin C acylase from *Pseudomonas diminuta* N-176 is disclosed as well as the recombinant production of this enzyme in *E. coli*. The enzyme is characterized by the ability to catalyze the conversion of cephalosporin C, gultaryl 7-ACA, apidyl 7-ACA, succinyl 7-ACA, N-acetylcephalosporin C, N-benzoylcephalosporin C, and cephalothin into 7-aminocephalosporanic acid and is composed of an α-subunit with a molecular weight of 26,000 daltons and a β-subunit with a molecular weight of 58,000 daltons.

2 Claims, 11 Drawing Sheets

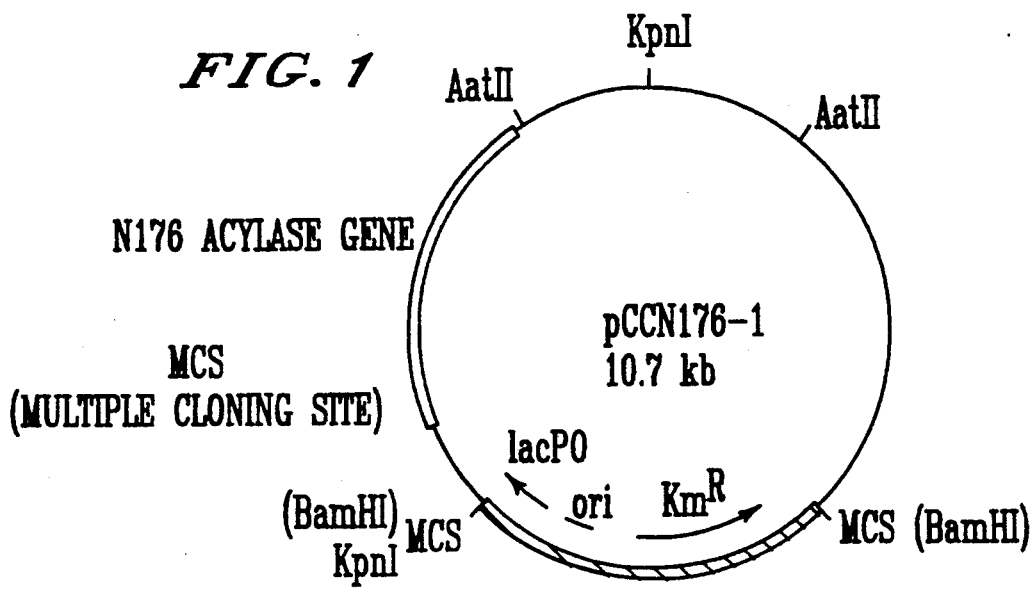
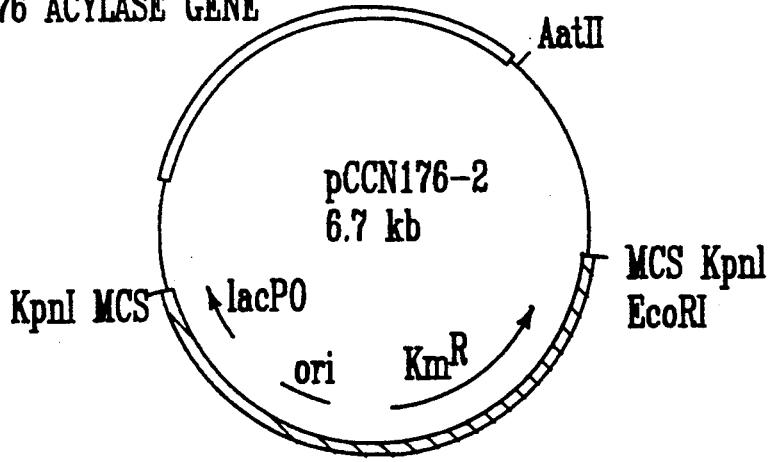
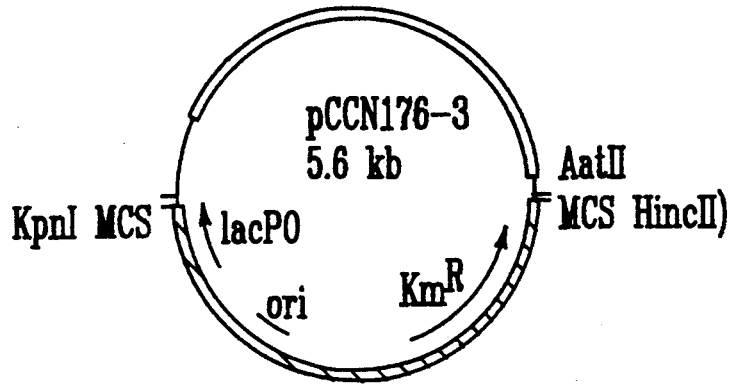
FIG. 1

```
CCCGGGGATC TCGCAGACGG CTGGCGCGGT CCTGGCCAGC AATATGCGCA AGGCCGGCTT   60
CACGGTGGAA GAGCAGGTGA TGGATTGGGG CACGGTGCTC GCCCGCCGGG CCAAGAAGGA  120
CGGCTGGAGC GTTTTCCCGG TCTACGCCAA CGGCATCGAC ATGATGTCGC CGCTGACGCA  180
TTTCTACATC GGCAACAACT GCGTGAACTA TGCGGGCTGG AGCTGCGACG CCGTCATCAC  240
CGAAAAGCTC GCCGCCTATG CCAAGGCGCC CGATCCGGCT ACCCGCAAAC GCATCGCGGC  300
CGAAATCCAG GTCGAGGCCT ACAAGGACAC GCCCTCCGTG ATGTGGGGCC AGTTCAGCCG  360
GCCGGCGGGC TACCGCCTGC GCCTCAAGAA CATCGTCCAG TCCAGCTTCC CGATCTTCTG  420
GCAGCTCACG CTCGACGCGT GAGCTTGCCC AGATTCCGAC AAGCAATGAG GTCCCGACGC  480
```

| | | | | | | | | | | | | | | | | |
|---|---|---|---|---|---|---|---|---|---|---|---|---|---|---|---|---|
| GA | ATG | ACT | ATG | GCG | GCC | AAC | ACC | GAT | CGC | GCG | GTC | TTG | CAG | GCG | GCG | 527 |
| | Met | Thr | Met | Ala | Ala | Asn | Thr | Asp | Arg | Ala | Val | Leu | Gln | Ala | Ala | |
| | 1 | | | 5 | | | | | | 10 | | | | | | |
| CTG | CCG | CCG | CTT | TCC | GGC | AGC | CTC | CCC | ATT | CCC | GGA | TTG | AGC | GCG | TCG | 575 |
| Leu | Pro | Pro | Leu | Ser | Gly | Ser | Leu | Pro | Ile | Pro | Gly | Leu | Ser | Ala | Ser | |
| 15 | | | | 20 | | | | | 25 | | | | | 30 | | |
| GTC | CGC | GTC | CGG | CGC | GAT | GCC | TGG | GGC | ATC | CCG | CAT | ATC | AAG | GCC | TCG | 623 |
| Val | Arg | Val | Arg | Arg | Asp | Ala | Trp | Gly | Ile | Pro | His | Ile | Lys | Ala | Ser | |
| | | | 35 | | | | | 40 | | | | | 45 | | | |
| GGC | GAG | GCC | GAT | GCC | TAT | CGG | GCG | CTG | GGC | TTC | GTC | CAT | TCG | CAG | GAC | 671 |
| Gly | Glu | Ala | Asp | Ala | Tyr | Arg | Ala | Leu | Gly | Phe | Val | His | Ser | Gln | Asp | |
| | | 50 | | | | | 55 | | | | | 60 | | | | |
| CGT | CTT | TTC | CAG | ATG | GAG | CTG | ACG | CGT | CGC | AAG | GCG | CTG | GGA | CGC | GCG | 719 |
| Arg | Leu | Phe | Gln | Met | Glu | Leu | Thr | Arg | Arg | Lys | Ala | Leu | Gly | Arg | Ala | |
| | 65 | | | | 70 | | | | | 75 | | | | | | |
| GCC | GAA | TGG | CTG | GGC | GCC | GAG | GCC | GCC | GAG | GCC | GAT | ATC | CTC | GTG | CGC | 767 |
| Ala | Glu | Trp | Leu | Gly | Ala | Glu | Ala | Ala | Glu | Ala | Asp | Ile | Leu | Val | Arg | |
| 80 | | | | | 85 | | | | | 90 | | | | | | |
| CGG | CTC | GGA | ATG | GAA | AAA | GTC | TGC | CGG | CGC | GAC | TTC | GAG | GCC | TTG | GGC | 815 |
| Arg | Leu | Gly | Met | Glu | Lys | Val | Cys | Arg | Arg | Asp | Phe | Glu | Ala | Leu | Gly | |
| 95 | | | | | 100 | | | | | 105 | | | | | 110 | |
| GTC | GAG | GCG | AAG | GAC | ATG | CTG | CGG | GCT | TAT | GTC | GCC | GGC | GTG | AAC | GCA | 863 |
| Val | Glu | Ala | Lys | Asp | Met | Leu | Arg | Ala | Tyr | Val | Ala | Gly | Val | Asn | Ala | |
| | | | 115 | | | | | 120 | | | | | 125 | | | |
| TTC | CTG | GCT | TCC | GGT | GCT | CCC | CTG | CCT | GTC | GAA | TAC | GGA | TTG | CTC | GGA | 911 |
| Phe | Leu | Ala | Ser | Gly | Ala | Pro | Leu | Pro | Val | Glu | Tyr | Gly | Leu | Leu | Gly | |
| | 130 | | | | | 135 | | | | | 140 | | | | | |

*FIG. 2a*

```
GCA GAG CCG GAG CCC TGG GAG CCT TGG CAC AGC ATC GCG GTG ATG CGC      959
Ala Glu Pro Glu Pro Trp Glu Pro Trp His Ser Ile Ala Val Met Arg
        145             150             155

CGG CTG GGC CTG CTT ATG GGT TCG GTG TGG TTC AAG CTC TGG CGG ATG     1007
Arg Leu Gly Leu Leu Met Gly Ser Val Trp Phe Lys Leu Trp Arg Met
    160             165             170

CTG GCG CTG CCG GTG GTC GGA GCC GCG AAT GCG CTG AAG CTG CGC TAT     1055
Leu Ala Leu Pro Val Val Gly Ala Ala Asn Ala Leu Lys Leu Arg Tyr
175             180             185             190

GAC GAT GGC GGC CGG GAT TTG CTC TGC ATC CCG CCG GGC GCC GAA GCC     1103
Asp Asp Gly Gly Arg Asp Leu Leu Cys Ile Pro Pro Gly Ala Glu Ala
                195             200             205

GAT CGG CTC GAG GCG GAT CTC GCG ACC CTG CGG CCC GCG GTC GAT GCG     1151
Asp Arg Leu Glu Ala Asp Leu Ala Thr Leu Arg Pro Ala Val Asp Ala
            210             215             220

CTG CTG AAG GCG ATG GGC GGC GAT GCC TCC GAT GCT GCC GGC GGC GGC     1199
Leu Leu Lys Ala Met Gly Gly Asp Ala Ser Asp Ala Ala Gly Gly Gly
        225             230             235

AGC AAC AAC TGG GCG GTC GCT CCG GGC CGC ACG GCG ACC GGC AGG CCG     1247
Ser Asn Asn Trp Ala Val Ala Pro Gly Arg Thr Ala Thr Gly Arg Pro
    240             245             250

ATC CTC GCG GGC GAT CCG CAT CGC GTC TTC GAA ATC CCG GGC ATG TAT     1295
Ile Leu Ala Gly Asp Pro His Arg Val Phe Glu Ile Pro Gly Met Tyr
255             260             265             270

GCG CAG CAT CAT CTG GCC TGC GAC CGG TTC GAC ATG ATC GGC CTG ACC     1343
Ala Gln His His Leu Ala Cys Asp Arg Phe Asp Met Ile Gly Leu Thr
                275             280             285

GTG CCG GGC GTG CCG GGC TTC CCG CAC TTC GCG CAT AAC GGC AAG GTC     1391
Val Pro Gly Val Pro Gly Phe Pro His Phe Ala His Asn Gly Lys Val
            290             295             300

GCC TAT TGC GTC ACC CAT GCC TTC ATG GAC ATC CAC GAT CTC TAT CTC     1439
Ala Tyr Cys Val Thr His Ala Phe Met Asp Ile His Asp Leu Tyr Leu
        305             310             315
```

*FIG. 2b*

```
GAG CAG TTC GCG GGG GAG GGC CGC ACT GCG CGG TTC GGC AAC GAT TTC      1487
Glu Gln Phe Ala Gly Glu Gly Arg Thr Ala Arg Phe Gly Asn Asp Phe
    320             325             330

GAG CCC GTC GCC TGG AGC CGG GAC CGT ATC GCG GTC CGG GGT GGC GCC      1535
Glu Pro Val Ala Trp Ser Arg Asp Arg Ile Ala Val Arg Gly Gly Ala
335             340             345

GAT CGC GAG TTC GAT ATC GTC GAG ACG CGC CAT GGC CCG GTT ATC GCG      1583
Asp Arg Glu Phe Asp Ile Val Glu Thr Arg His Gly Pro Val Ile Ala
                355             360             365

GGC GAT CCG CGC GAT GGC GCA GCG CTC ACG CTG CGT TCG GTC CAG TTC      1631
Gly Asp Pro Arg Asp Gly Ala Ala Leu Thr Leu Arg Ser Val Gln Phe
        370             375             380

GCC GAG ACC GAT CTG TCC TTC GAC TGC CTG ACG CGG ATG CCG GGC GCA      1679
Ala Glu Thr Asp Leu Ser Phe Asp Cys Leu Thr Arg Met Pro Gly Ala
            385             390             395

TCG ACC GTG GCC CAG CTC TAC GAC GCG ACG CGC GGC TGG GGC CTG ATC      1727
Ser Thr Val Ala Gln Leu Tyr Asp Ala Thr Arg Gly Trp Gly Leu Ile
    400             405             410

GAC CAT AAC CTC GTC GCC GGG GAT GTC GCG GGC TCG ATC GGC CAT CTG      1775
Asp His Asn Leu Val Ala Gly Asp Val Ala Gly Ser Ile Gly His Leu
415             420             425             430

GTC CGC GCC CGC GTT CCG TCC CGT CCG CGC GAA AAC GGC TGG CTG CCG      1823
Val Arg Ala Arg Val Pro Ser Arg Pro Arg Glu Asn Gly Trp Leu Pro
                435             440             445

GTG CCG GGC TGG TCC GGC GAG CAT GAA TGG CGG GGC TGG ATT CCG CAC      1871
Val Pro Gly Trp Ser Gly Glu His Glu Trp Arg Gly Trp Ile Pro His
        450             455             460

GAG GCG ATG CCG CGC GTG ATC GAT CCG CCG GGC GGC ATC ATC GTC ACG      1919
Glu Ala Met Pro Arg Val Ile Asp Pro Pro Gly Gly Ile Ile Val Thr
            465             470             475

GCG AAT AAT CGC GTC GTG GCC GAT GAC CAT CCC GAT TAT CTC TGC ACC      1967
Ala Asn Asn Arg Val Val Ala Asp Asp His Pro Asp Tyr Leu Cys Thr
    480             485             490
```

*FIG. 2c*

```
GAT TGC CAT CCG CCC TAC CGC GCC GAG CGC ATC ATG AAG CGC CTG GTC    2015
Asp Cys His Pro Pro Tyr Arg Ala Glu Arg Ile Met Lys Arg Leu Val
495             500             505             510

GCC AAT CCG GCT TTC GCC GTC GAC GAT GCC GCC GCG ATC CAT GCC GAT    2063
Ala Asn Pro Ala Phe Ala Val Asp Asp Ala Ala Ala Ile His Ala Asp
                515             520             525

ACG CTG TCG CCC CAT GTC GGG TTG CTG CGC CGG AGG CTC GAG GCG CTT    2111
Thr Leu Ser Pro His Val Gly Leu Leu Arg Arg Arg Leu Glu Ala Leu
            530             535             540

GGA GCC CGC GAC GAC TCC GCG GCC GAA GGG CTG AGG CAG ATG CTC GTC    2159
Gly Ala Arg Asp Asp Ser Ala Ala Glu Gly Leu Arg Gln Met Leu Val
        545             550             555

GCC TGG GAC GGC CGC ATG GAT GCG GCT TCG GAG GTC GCG TCT GCC TAC    2207
Ala Trp Asp Gly Arg Met Asp Ala Ala Ser Glu Val Ala Ser Ala Tyr
    560             565             570

AAT GCG TTC CGC AGG GCG CTG ACG CGG CTG GTG ACG GAC CGC AGC GGG    2255
Asn Ala Phe Arg Arg Ala Leu Thr Arg Leu Val Thr Asp Arg Ser Gly
575             580             585             590

CTG GAG CAG GCG ATA TCG CAT CCC TTC GCG GCT GTC GCG CCG GGC GTC    2303
Leu Glu Gln Ala Ile Ser His Pro Phe Ala Ala Val Ala Pro Gly Val
            595             600             605

TCA CCG CAA GGC CAG GTC TGG TGG GCC GTG CCG ACC CTG CTG CGC GAC    2351
Ser Pro Gln Gly Gln Val Trp Trp Ala Val Pro Thr Leu Leu Arg Asp
        610             615             620

GAC GAT GCC GGA ATG CTG AAG GGC TGG AGC TGG GAC CAG GCC TTG TCT    2399
Asp Asp Ala Gly Met Leu Lys Gly Trp Ser Trp Asp Gln Ala Leu Ser
    625             630             635

GAG GCC CTC TCG GTC GCG TCG CAG AAC CTG ACC GGG CGA AGC TGG GGC    2447
Glu Ala Leu Ser Val Ala Ser Gln Asn Leu Thr Gly Arg Ser Trp Gly
640             645             650

GAA GAG CAT CGG CCG CGC TTC ACG CAT CCG CTT GCC ACG CAA TTC CCG    2495
Glu Glu His Arg Pro Arg Phe Thr His Pro Leu Ala Thr Gln Phe Pro
655             660             665             670
```

*FIG. 2d*

```
GCC TGG GCG GGG CTG CTG ATT CCG GCT TCC CGT CCG ATC GGT GGC GAT    2543
Ala Trp Ala Gly Leu Leu Asn Pro Ala Ser Arg Pro Ile Gly Gly Asp
                675                 680                 685

GGC GAT ACC GTG CTG GCG AAC GGG CTC GTC CCG TCA GCC GGG CCG CAG    2591
Gly Asp Thr Val Leu Ala Asn Gly Leu Val Pro Ser Ala Gly Pro Gln
                690                 695                 700

GCG ACC TAT GGT GCC CTG TCG CGC TAC GTC TTC GAT GTC GGC AAT TGG    2639
Ala Thr Tyr Gly Ala Leu Ser Arg Tyr Val Phe Asp Val Gly Asn Trp
                705                 710                 715

GAC AAT AGC CGC TGG GTC GTC TTC CAC GGC GCC TCC GGG CAT CCG GCC    2687
Asp Asn Ser Arg Trp Val Val Phe His Gly Ala Ser Gly His Pro Ala
    720                 725                 730

AGC GCC CAT TAT GCC GAT CAG AAT GCG CCC TGG AGC GAC TGT GCG ATG    2735
Ser Ala His Tyr Ala Asp Gln Asn Ala Pro Trp Ser Asp Cys Ala Met
735                 740                 745                 750

GTG CCG ATG CTC TAT AGC TGG GAC AGG ATC GCG GCA GAG GCC GTG ACG    2783
Val Pro Met Leu Tyr Ser Trp Asp Arg Ile Ala Ala Glu Ala Val Thr
                755                 760                 765

TCG CAG GAA CTC GTC CCG GCC TGAGGGCCGG GCCTGTTGTC AGCCTGCCGC       2834
Ser Gln Glu Leu Val Pro Ala
                770

AGCTCTCTTC GGC                                                     2847
```

*FIG. 2e*

CEPHALOSPORIN C ACYLASE

The invention relates to a new cephalosporin C acylase (hereinafter referred to as "CC acylase N-176"). More particularly, it relates to a new CC acylase derived from *Pseudomonas diminuta* N-176, a DNA encoding thereof, an expression vector containing said DNA, a microorganism transformed with said expression vector, and the production of the CC acylase by culturing said transformant.

Cephalosporin C acylase is a general term for an enzyme, which is, in common, capable of hydrolyzing cephalosporin C to 7-aminocephalosporanic acid 7-ACA). 7-ACA has been made by methods of chemical conversion of cephalosporin C such as iminoether or nitrosyl chloride method. However, to make cost reduction, an alternative method utilizing enzymatic conversion has been searched for a long time since similar enzymatic conversion was successfully adopted for the production of 6-aminopenicillanic acid (6-APA) which is a starting material for penicillins, another family of β-lactam antibiotics. In the course of such efforts, two step enzymatic conversion was devised using D-amino acid oxidase and glutaryl 7-ACA (GL 7-ACA) acylase. This method has been industrialized as the one where the enzymatic oxidation was substituted by chemical oxidation. This two step method was an offspring to overcome the difficulty of discovering acylases which can convert cephalosporin C directly to 7-ACA.

However, since advantage of one step conversion over the two step one was apparent, extensive studies for searching such an enzyme named cephalosporin C acylase has still been continued thereafter. Recently, cephalosporin C acylases were definitely clarified to be produced by Pseudomonas species (Cf. Japanese Patent Applications Laid Open Nos. 61-152286 and 62-48380).

The inventors of this invention have conducted extensive studies for searching new CC acylases, and as the results, the present inventors have been found a new characteristic CC acylase N-176 in the cultured broth of a newly isolated organism, *Pseudomonas diminuta* N-176 and established industrial production of this enzyme. The CC acylase N-176 of this invention, as compared with prior CC acylases, is characterized by higher stability, higher enzymatic potency and the like, and further characteristics of this CC acylase will be apparent from the description mentioned below.

A strain named *Pseudomonas diminuta* N-176 which is a cephalosporin C acylase producer was newly isolated from a soil sample collected in Aomori Prefecture, Japan. A culture of the living organism has been deposited with Fermentation Research Institute, Agency of Industrial Science and Technology, 1-3, Higashi 1 chome Tsukubashi Ibaraki-ken 305 Japan under the number FERM-BP 3046 on Aug. 7, 1990.

*Pseudomonas diminuta* N-176 has the following morphological and physiological characteristics and identified as *Pseudomonas diminuta* according to Bergey's Manual of Systematic Bacteriology (Volume 1) and in the result of the comparative experiment using *Pseudomonas diminuta* ATCC 19146. The method described in Bergey's Manual was employed principally for this taxonomic study.

1. Morphological characteristics

Morphological observation of the strain N-176 was carried out by the optical microscope with cells grown in Trypticase soy broth (BBL Co., Ltd., U.S.A.) at 37° C.

Strain N-176 was a gram-negative, motile bacterium. The cell shapes were rod. Results are shown in Table 1.

TABLE 1

| Morphological characteristics of strain N-176 | |
|---|---|
| Gram stain | negative |
| color of colony | gray |
| cell shape | rod |
| spore | negative |
| motility | positive |
| flagella | single polar flagellum |

2. Physiological Characteristics

Physiological characteristics of the strain N-176 were summarized in Table 2.

The strain N-176 was oxidase positive, catalase positive and O-F test negative. Gelatin was not liquefied and esculin hydrolysis was negative. None of the carbohydrates tested were fermented. Indole test was negative. Voges-Proskauer test was negative.

TABLE 2

| Physiological characteristics of the strain N-176 | |
|---|---|
| Conditions | Characteristics |
| growth in air | + |
| in anaerobe | − |
| at 8° C. | − |
| at 30° C. | + |
| at 37° C. | + |
| at 40° C. | − |
| pigment | − |
| catalase | +w |
| oxidase | +w |
| OF-tst | − |
| TSI | −/− |
| IPA | − |
| H$_2$S (SIM medium) | − |
| H$_2$S (lead acetate) | − |
| indole | − |
| VP | − |
| Simmons' citrate | − |
| urease (Christensen) | +w |
| gelatin liquefection | − |
| esculin hydrolysis | − |
| nitrate reduction/gas | +/− |
| lysine decarboxylase | − |
| ornithine decarboxylase | − |
| arginine dihydrolase | − |
| acylamidase | − |
| utilization of arabinose dulcitol | − |
| glucose | − |
| galactose | − |
| ethanol | − |
| inositol | − |
| lactose | − |
| maltose | − |
| mannose | − |
| rhamnose | − |
| starch | − |
| sucrose | − |
| trehalose | − |
| xylose | − |
| lecithinase (egg yolk) | − |

Note: +; positive, −; negative, +w; weakly positive

The new CC acylase of this invention has the following characteristics.

Namely, the new CC acylase of this invention
(a) has the ability to catalyze the enzymatic conversion of cephalosporin C, glutaryl 7-ACA, adipyl 7-ACA, succinyl 7-ACA, N-acetylcephalosporin C, N-benzoylcephalosporin C and cephalothin into 7-amino cephalosporanic acid, (b) is composed of α-subunit [Molecular weight: 26,000 dalton (SDS-PAGE)] and α-subunit [Molecular weight: 58,000 dalton (SDS-PAGE)] and (c) has N-terminal amino acid sequence (SER ID NO:1) of the α-subunit: Thr-Met-Ala-Ala-Asn-Thr-Asp-Arg-Ala-Val-Leu-Gln-Ala-Ala-Leu-Pro-Pro-Leu-.

The new CC acylase of this invention can be prepared by recombinant DNA technology, polypeptide synthesis and the like.

Namely, the new CC acylase can be prepared by culturing a host cell transformed with an expression vector comprising DNA encoding amino acid sequence of the new CC acylase in a nutrient medium and recovering the new CC acylase from the cultured broth.

In this process, particulars of which are explained in more detail as follows.

The host cell may include microorganisms [bacteria (e.g. *Escherichia coli, Bacillus subtills*, etc.), yeast (e.g. *Saccharomyces cerevisiae*, etc.), animal cell lines and cultured plant cells]. Preferred examples of the microorganism may include bacteria, especially a strain belonging to the genus Escherichia (e.g. *E. coli* JM109 ATCC 53323, *E. coli* HB101 ATCC 33694, E. coli HB101-16 FERM BP-1872, *E. coli* 294 ATCC 31446, etc.), yeast, especially a strain belonging to the genus Saccharomyces [e.g. *Saccharomyces cerevisiae* AH22], animal cell lines [e.g. mouse L929 cell, Chinese hamster ovary (CHO) cell etc.] and the like.

When bacterium, especially *E. coli* is used as a host cell, the expression vector is usually composed of at least promoter-operator region, initiation codon, DNA encoding amino acid sequence of the new CC acylase, termination codon, terminator region and replicatable unit. When yeasts or animal cells are used as host cells, the expression vector is preferably composed of at least promoter, initiation codon, DNA encoding amino acid sequences of the signal peptide and the new CC acylase and termination codon, and it is possible that enhancer sequence, 5'- and 3'-noncoding region of the new CC acylase, splicing junctions, polyadenylation site and replicatable unit are also inserted into the expression vector.

The promoter-operator region comprises promoter, operator and Shine-Dalgarno (SD) sequence (e.g. AAGG, etc.). Preferable promoter-operator region may include conventionally employed promoter-operator region (e.g. PL-promoter and trp-promoter for *E. coli*) and promoter of the CC acylase N-176 chromosomal gene. The promoter for expression of the new CC acylase in yeast may include the promoter of the TRPl gene, the ADHI or ADHII gene and acid phosphatase (pHO5) gene for *S. cerevisiae* and the promoter for expression of the new CC acylase in mammalian cells may include SV40 early or late-promoter, HTLV-LTR-promoter, mouse metallothionein I(MMT)-promoter, vaccinia-promoter and the like.

Preferable initiation codon may include methionine codon (ATG).

The signal peptide may include a signal peptide of conventionally employed other enzymes (signal peptide of the native t-PA, signal peptide of the native plasminogen) and the like.

The DNA encoding amino acid sequence of the signal peptide or the new CC acylase can be prepared in a conventional manner such as a partial or whole DNA synthesis using DNA synthesizer and/or treatment of the complete DNA sequence coding for the new CC acylase inserted in a suitable vector [e.g. PCCN 176-2] obtainable from a transformant [e.g. *E. coli* JM109 (PCCN 176-2)FERM BP-3047] with a suitable enzyme (e.g. restriction enzyme, alkaline phosphatase, polynucleotide kinase, DNA ligase, DNA polymerase, etc.).

The termination codon(s) may include a conventionally employed termination codon (e.g. TAG, TGA, etc.).

he terminator region may include natural or synthetic terminator [e.g. synthetic fd phage terminator, etc.).

The replicatable unit is a DNA compound having capable of replicating the whole DNA sequence belonging thereto in a host cell and may include natural plasmid, artificially modified plasmid (e.g. DNA fragment prepared from natural plasmid) and synthetic plasmid and preferable examples of the plasmid may include plasmid pBR322 or artificially modified thereof (DNA fragment obtained from a suitable restriction enzyme treatment of pBR322) for *E. coli*, yeast 2μ plasmid or yeast chromosomal DNA for yeast, plasmid pRSVneo ATCC 37198, plasmid pSV2dhfr ATCC 37145, plasmid pdBPV-MMTneo ATCC 37224, plasmid pSV2neo ATCC 37149 for mammalian cells.

The enhancer sequence may include the enhancer sequence (72 b.p.) of SV40.

The polyadenylation site may include the polyadenylation site of SV40.

The splicing junction may include the splicing junction of SV40.

The promoter, initiation codon, DNA encoding amino acid sequence of the new CC acylase, termination codon(s) and terminator region can consecutively and circularly be linked with an adequate replicatable unit (plasmid) together, if desired, using an adequate DNA fragment(s) (e.g. linker, other restriction site, etc.) in a conventional manner (e.g. digestion with restriction enzyme, ligation using T4 DNA ligase) to give an expression vector. When mammalian cells are used as host cells, it is possible that enhancer sequence, promoter, 5'-noncoding region of the cDNA of the new CC acylase, initiation codon, DNA encoding amino acid sequences of the signal peptide and the new CC acylase, termination codon(s), 3'-noncoding region of the cDNA of the new CC acylase, splicing junctions and polyadenylation site are consecutively and circularly be liked with an adequate replicatable unit together in the above manner.

A host cell can be transformed (transfected) with the expression vector. Transformation (transfection) can be carried out in a conventional manner [e.g. Kushner method for *E. coli*, calcium phosphate method for mammalian cells, microinjection, etc.] to give a transformant (transfectant).

For the production of the new CC acylase in the process of this invention, thus obtained transformant comprising the expression vector is cultured in an aqueous nutrient medium.

The nutrient medium may contain carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extract, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin $B_1$), antibiotics (e.g. ampicillin, kanamycin), etc.] may be added to the medium. For the culture of mammalian cells, Dulbecco's Modified Eagle's Minimum Essential Medium (DMEM)supplemented with fetal calf serum and an antibiotic is often used.

The culture of the transformant (including transfectant) may usually be carried out at pH 5.5-8.5 (preferably pH 7-7.5) and 18°-40° C. (preferably 25°-38° C.) for 5-50 hours.

When thus produced new CC acylase exists in the culture solution, culture filtrate (supernatant) is obtained by filtration or centrifugation of the cultured broth. From the culture filtrate, the new CC acylase can be purified in a conventional manner as generally employed for the purification and isolation of natural or synthetic proteins (e.g. dialysis, gel filtration, affinity column chromatography using anti-CC acylase monoclonal antibody, column chromatography on a suitable adsorbent, high performance liquid chromatography, etc.). When the produced new CC acylase exists in periplasm and cytoplasm of the cultured transformant, the cells are collected by filtration and centrifugation, and the cell wall and/or cell membrane thereof are destroyed by, for example, treatment with super sonic waves and/or lysozyme to give debris. The debris can be dissolved in a suitable aqueous solution (e.g. 8M aqueous urea, 6M aqueous guanidium salts). From the solution, the new CC acylase can be purified in a conventional manner as exemplified above.

if it is necessary to refold the new CC acylase produced in E. coli, the refolding can be carried out in a conventional manner.

This invention further provides a process for the preparation of a compound of the formula:

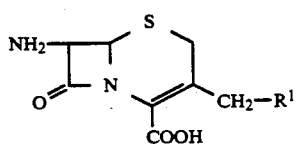

(I)

wherein $R^1$ is acetoxy, hydroxy and hydrogen or its salt, which comprises contacting a compound of the formula:

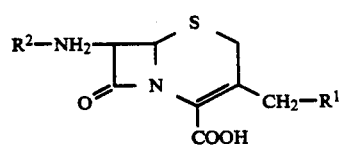

(II)

wherein
$R^1$ is the same as defined above and
$R^2$ is carboxylic acyl, or its salt, with the cultured broth of a microorganism transformed with an expression vector comprising DNA encoding the new CC acylase of this invention or its processed material.

The carboxylic acyl for $R^2$ may include aliphatic, aromatic or heterocyclic carboxylic acyl and suitable example thereof may be $C_1-C_6$ alkanoyl which may have one or two suitable substituent(s) selected from the group of amino, carboxy, $C_1-C_6$ alkanoylamino, benzamido or thienyl and the like.

Suitable salt of the compounds (I) and (II) may be alkali metal salt (e.g. sodium salt, potassium salt).

If the CC acylase activity usually exists in transformed cells, the following preparations can be exemplified as a processed material of the cultured broth.
(1) Raw cells; separated from the cultured broth in conventional manners such as filtration and centrifugation
(2) dried cells; obtained by drying said raw cells in conventional manners such as lyophilization and vacuum drying
(3) cell-free extract; obtained by destroying said raw or dried cells in conventional manners (e.g. autolysis of the cells using an organic solvent, grinding the cells with alumina, sea sand, etc. or treating the cells with super sonic waves)
(4) enzyme solution; obtained by purification or partial purification of said cell-free extracts in conventional manners (e.g. column chromatography)
(5) immobilized cells or enzyme; prepared by immobilizing said cells or enzyme in conventional manners (e.g. a method using acrylamide, glass bead, ion exchange resin, etc.).

The reaction comprising a contact of the compound (II) with the enzyme can be conducted in an aqueous medium such as water or a buffer solution, that is, it can be usually conducted by dissolving or suspending the cultured broth or its processed material in an aqueous medium such as water or a buffer solution containing the compound (II).

Preferable pH of the reaction mixture, concentration of the compound (II), reaction time and reaction temperature may vary with properties of a cultured broth or its processed material to be used. Generally, the reaction is carried out at pH 6 to 9, preferably pH 7 to 9, at 5° to 40° C., preferably 5° to 37° C. for 2 to 50 hours.

The concentration of the compound (II) as a substrate in the reaction mixture may be preferably selected from a range of 1 to 100 mg/ml.

Thus produced compound (I) can be purified and isolated from the reaction mixture in a conventional manner.

Brief explanation of the accompanying drawings is as follows.

FIG. 1 shows restriction site and function map of plasmids pCCN 176-1, pCCN 176-2 and pCCN 176-3. In this Figure, the abbreviation "MCS" means multiple cloning site.

FIGS. 2a-e show nucleotide sequence (SER ID NO:2) and deduced amino acid sequence (SER ID NO:3) of the CC acylase N-176 chromosomal gene. In the numbering of the DNA, the first nucleotide of the coding region is designated as +1.

Figure 5A:
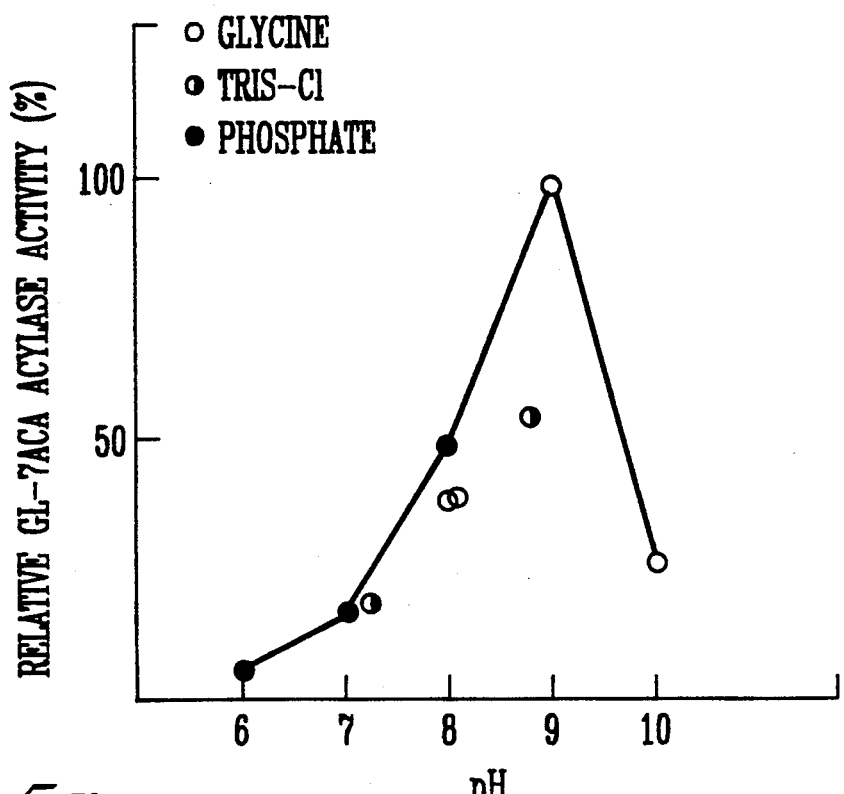

FIGS. 5a and b show optimum pH of the CC acylase N-176.

Figure 6:
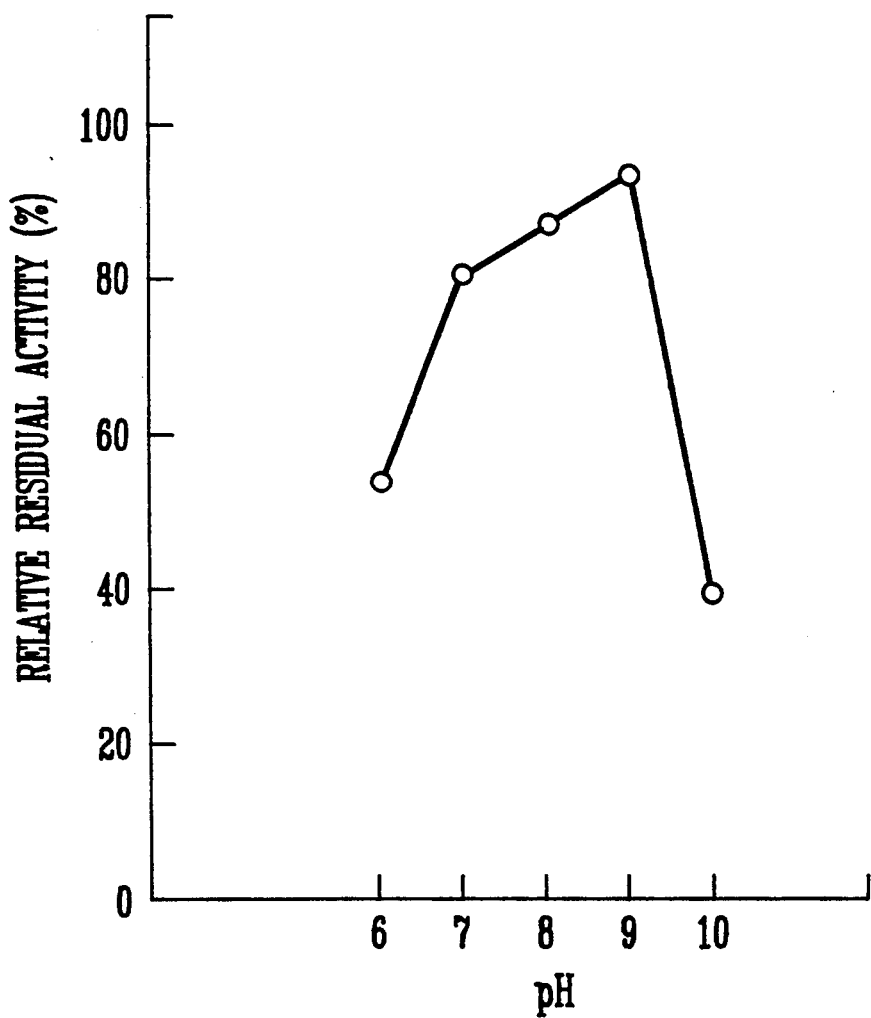

FIG. 6 shows pH profile of stability of the CC acylase N-176.

Figure 7A:
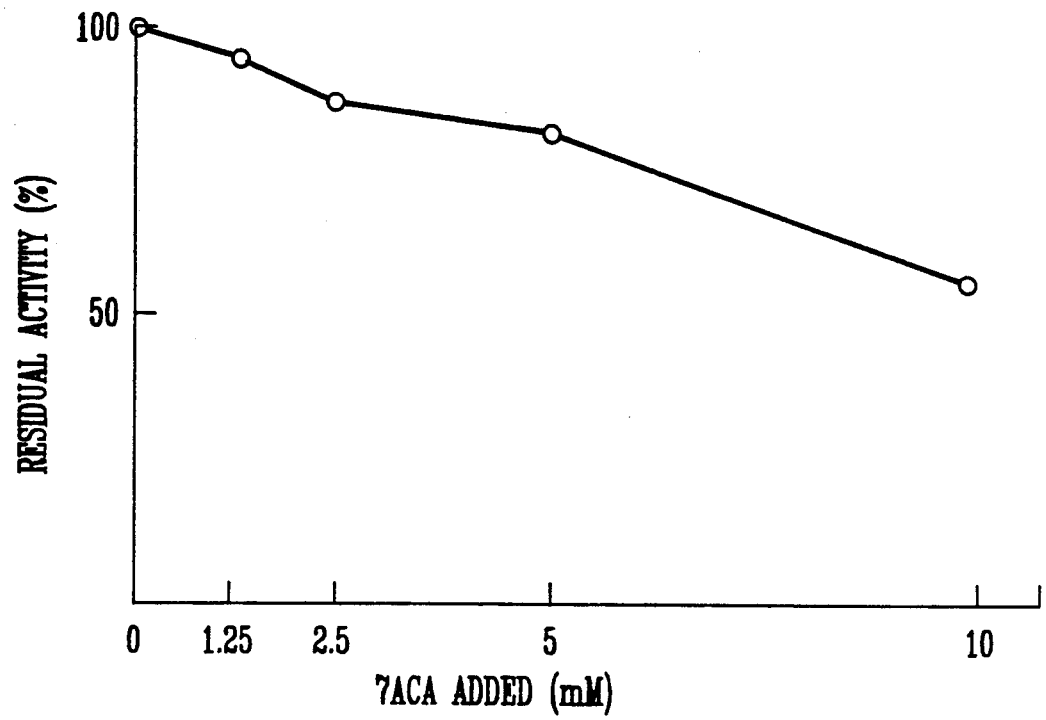

FIGS. 7a and b show inhibition of GL-7ACA acylase activity of the CC acylase N-176 by reaction products.

Figure 8A:
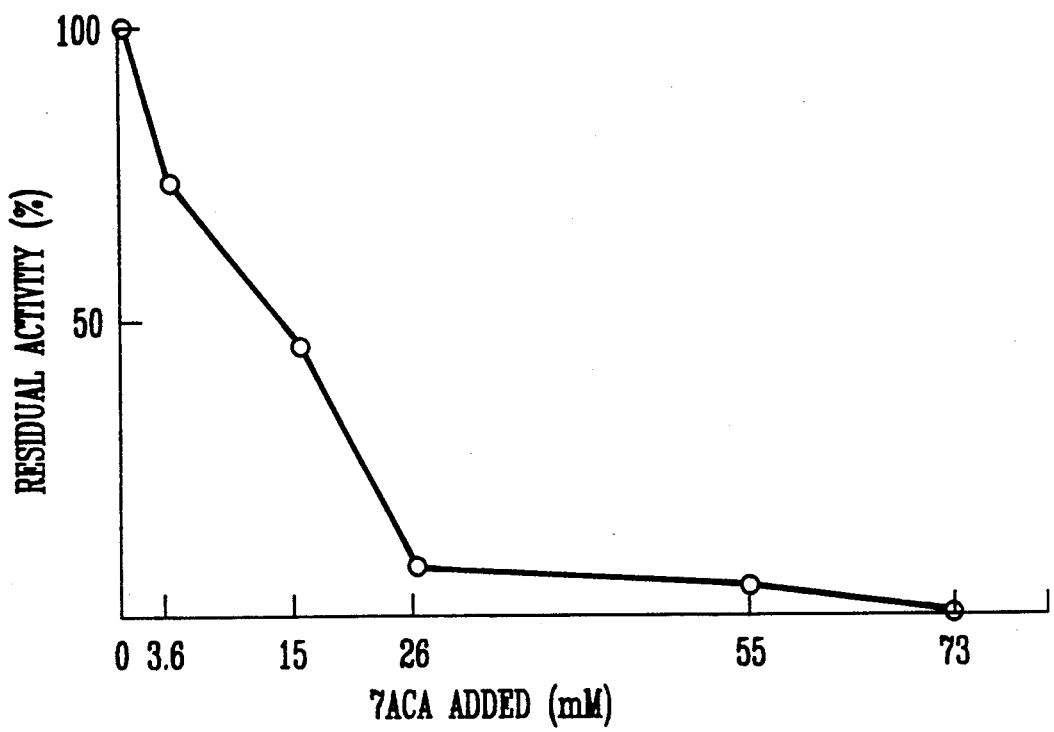

FIGS. 8a and b show inhibition of cephalosporin C acylase activity of the CC acylase N-176 by reaction products.

In the following Examples, some plasmids, enzymes, such as restriction enzymes, T4 DNA ligases, and other materials were obtained from commercial sources and used according to the indication by suppliers. Operations employed for the cloning of DNA, transformation of host cells, cultivation of transformants, recovery of the new CC acylase from the cultured broth, and the like are well known in the art or can be adapted from literatures.

Following examples are given for the purpose of illustrating this invention, but not limited thereto.

EXAMPLE 1

Isolation of the gene encoding cephalosporin C acylase of Pseudomonas diminuta N-176

1.1 Preparation of chromosomal DNA of Pseudomonas diminuta N-176

Chromosomal DNA of *Pseudomonas diminuta* N-176 was prepared according to the method of Harris-Warrick et al., Proc. Natl. Acad. Sci., USA 72: 2207–2211, 1975. *Pseudomonas diminuta* N-176 was grown with shaking at 30° C. for 40 hours in 3 l of meat extract broth (polypeptone 0.5%, sodium glutamate 0.5%, meat extract 0.2%, $MgSO_4.7H_2O$ 50 µg/ml), harvested by centrifugation and washed once with 50 mM Tris-HCl (pH 8) containing 1 mM EDTA. Resultant cell pellets [approximately 5 g (wet weight)] was suspended in 12.5 ml of 50 mM Tris-HCl (pH 8) containing 20% sucrose and 1 mM EDTA and treated with 12.5 mg of lysozyme at 37° C. for 15 min. Furthermore, to this suspension, 30 ml of 100 mM EDTA (pH 9.6)-1% lauroyl sarcosylate and 10 ml of 5 mg/ml of pronase E were added and the resultant mixture was incubated at 50° C. for 2 hours. After addition of 1.25 g of CsCl to each 1 ml of the lysate, it was applied to equilibrium density gradient centrifugation. After centrifugation, chromosomal DNA fractions were pooled and dialyzed against 10 mM Tris-HCl (pH 8) containing 1 mM EDTA (TE buffer).

2. Construction of genomic DNA library of Pseudomonas diminuta N-176

Three hundred micrograms of chromosomal DNA of *Pseudomonas diminuta* N-176 was partially cleaved with 3.75 units of restriction endonuclease Sau3AI and the resultant DNA fragments were applied to a GEN-PAK DNA column (6.0 mm×50 mm, Waters, USA) and elution was performed with a linear gradient of NaCl [0.07–0.1M] in 25 mM phosphate buffer (pH 6) at a flow rate of 1.0 ml/min over 30 min. Fractions of DNA with an average size of 7–9 kilo bases (kb) were pooled and DNA was collected by ethanol precipitation and dissolved in TE buffer. 20 µg of the plasmid vector pHSG298 DNA (Takara Shuzo, Japan) was cleaved with BamHI (Takara Shuzo, Japan), followed by phenol extraction and ethanol precipitation The DNA was dissolved in 200 µl of 10 mM Tris-HCl (pH 8) containing 10 mM EDTA and incubated at 37° C. for 20 min with 1 unit of bacterial alkaline phosphatase (Takara Shuzo, Japan). The reaction mixture was treated with phenol extraction and ethanol precipitation and dissolved in 40 µl of TE buffer. Sau3AI partially cleaved chromosomal DNA fragments (20 µg) were ligated at 12° C. for 16 hours with 500 units of T4 DNA ligase (Takara Shuzo, Japan) to 5 µg of the linearized and dephosphorylated pHSG298. The ligation mixture was used for transformation of *E. coli* JM109 (Toyobo Co., Ltd., Japan). Transformation was performed according to the procedure of D. Hanahan (Cf. J. Mol. Biol. 166, 557–580 (1983)). The transformants were selected on LM agar containing trypton (Difco) 1%, yeast extract (Difco) 0.5%, sodium chloride 10 mM, magnesium sulfate 10 mM, agar 1.5% and 20 µg of kanamycin /ml. The number of transformants obtained was 24,000.

1.3. Selection of a clone possessing a plasmid containing a cephalosporin C acylase gene A clone possessing a plasmid containing cephalosporin C acylase gene was screened among the genomic DNA library of *Pseudomonas diminuta* N-176 by the following HPLC method. Transformant colonies were picked up and grown overnight at 30° C. in 1 ml of 2% Bouillon (Eiken Chemical Co., Ltd., Japan) supplemented with 1 mM isopropyl-β-D-galactoside (IPTG: Sigma Chemical Co., Ltd., U.S.A.). Cells were harvested by centrifugation and resulting cell pellets were used for assay. Reaction mixture (200 µl) containing 100 mM phosphate (pH 8), 2 mg of GL-7ACA or cephalosporin C Na and cell pellets were thoroughly mixed and incubated for 10 min at 37° C. The reaction was terminated by the addition of 200 µl of 4% acetic acid. Samples were applied to a Inertsil ODS-2 column (4.6 mm×150 mm)(Gasukuro Kogyo Co., Ltd., Japan) and elution was performed with 0.567 g/l of $Na_2PO_4$, 0.36 g/l of KH and 2–4% methanol. 7ACA was detected with absorption at 254 nm.

1.4. Subcloning of the gene encoding cephalosporin C acylase (Cf. FIG. 1)

Plasmid DNA was extracted from one of the positive clones by the cleared lysate method described by Clewell and Helinski (Cf. Proc. Natl. Acad. Sci., USA 61: 1159–1166, 1969) and named pCCN176-1. The size of the insert DNA was estimated to be approximately 8 kb by agarose gel electrophoresis. 10 µg of the recombinant plasmid pCCN176-1 DNA was cleaved with KpnI (Takara Shuzo, Japan) and 4 kb of the resulting DNA fragment of the insert was separated by agarose gel electrophoresis, eluted from the gel by electrophoresis, treated with phenol extraction and ethanol precipitation and dissolved in TE buffer. This DNA fragment of the insert of 1 µg was ligated with 25 units of T4 DNA ligase to 1 µg of pHSG299 DNA (Takara) linearized by digestion with KpnI. *E. coli* JM109 was transformed with this ligation mixture. Transformants were selected on LM agar plates containing 20 µg/ml of kanamycin and confirmed by criteria of loss of β-galactosidase activity, size of an insert and presence of cephalosporin C acylase. Activity of cephalosporin C acylase was measured by the HPLC method as described in Example 1.3. From one of the recombinant strain, plasmid DNA was extracted by the cleared lysate method and named pCCN176-2. 15 µg of pCCN176-2 was cleaved with EcoRI (Takara Shuzo, Japan), treated with phenol extraction and ethanol precipitation and dissolved in 336 µl of Ba131 buffer (20 mM Tris-HCl (pH 8), 600 mM NaCl, 12 mM $CaCl_2$, 12 mM MgCl and 1 mM EDTA). This linearized DNA was incubated at 30° C. with 30 units of Ba131 nuclease. Fifty µl of aliquots were sampled after 30 sec, 1, 2, 3, 4 and 5 min of incubation and the reaction was stopped by adding equal volume of phenol. After treatment of phenol and ethylether extraction and ethanol precipitation, Ba131 treated DNAs were dissolved in 20 mM Tris-HCl (pH 7.5) containing 10 mM $MgCl_2$ and 1 mM dithiothreitol (DTT) and incubated at room temperature for 30 min with 1 unit of Klenow fragment (Takara Shuzo, Japan) in the presence of 2 mM each of dATP, dCTP, dGTP, and dTTP (Kojin Co., Ltd., Japan). Reaction was terminated by phenol extraction, followed by ethylether extraction and ethanol precipitation. DNAs were dissolved in TE buffer and cleaved with KpnI. The KpnI cleaved DNA fragments with the size of 2.6–3 kb were isolated by agarose gel electrophoresis and ligated with T4 DNA ligase to pHSG298 DNA cleaved with KpnI and HincII (Takara Shuzo). The ligation mixture was used for transformation of E. coli JM 109. Transformants were selected and confirmed as described previously. Plasmid DNA was prepared from one of the positive transformants and named pCCN176-3, the size of insert of which was estimated to be approximately 2.9 kb.

EXAMPLE 2

Determination of nucleotide sequence of the gene encoding cephalosporin C acylase of Pseudomonas diminuta N-176

2.1. Determination of nucleotide sequence

Restriction endonuclease mapping of the insert of pCCN176-3 was performed using restriction endonucleases EcoRV, Eco47III, MluI, NcoI, SacII, SalI, SmaI and XhoI (All from Takara Shuzo). Appropriate restriction endonuclease cleaved DNA fragments were subcloned into M13 phage vector and used for determination of the nucleotide sequences. Nucleotide sequence was determined by the dideoxy chain termination method (Cf. Sanger et al. Proc. Natl. Acad. Sci., U.S.A. 74, 5463–5467 (1977)) using M13 sequencing kit (Toyobo Co., Ltd., Japan). The enzyme used was a modified T7 DNA polymerase (Sequenase) and both 7-deaza dGTP and dITP were separately adopted as the nucleotide analog. Primers with the size of 20 bases corresponding to the sequence located in the middle of DNA fragments to be sequenced were also used in addition to the universal primer. Gel electrophoresis was performed at 2200V for 5 or 13 hours using 5% polyacrylamide gel containing 7M urea of 80 cm long. The nucleotide sequence of the insert of pCCN176-3 was shown in FIG. 2. One open reading frame of 2322 bp was recognized. This open reading frame was confirmed as the gene encoding the cephalosporin C acylase of Pseudomonas diminuta N-176 by following two results.

1) The molecular weight of the cephalosporin C acylase (the sum of the molecular weights of $\alpha$ and $\beta$ subunits) estimated by SDS-polyacrylamide gel electrophoresis was well coincided with that calculated from the deduced amino acid sequences for the open reading frame.
2) The amino-terminal sequences of $\alpha$ and $\beta$ subunits of the cephalosporin C acylase determined by gas-sequencing method (details will be described in the next Example) were identical with the amino acid sequences between codons at positions 1 and 18 and between codons at positions 239 and 253.

2.2. Comparison of the amino acid sequence of the cephalosporin C acylase of Pseudomonas diminuta N-176 with that of Pseudomonas sp. SE83

The amino acid sequence of the cephalosporin C acylase of Pseudomonas diminuta N-176 was compared with the known one of Pseudomonas sp. SE83 (Cf. K. Komatsu et al., Japanese Patent Application laid open No.61-152286, A. Matsuda et al.; J. Bacteriol. 169, 5815–5820 (1987)). the number of amino acid residues of CC acylase N-176 was identical with that of SE83 acylase. However, 50 amino acid residues and 198 nucleotide residues were recognized to be different between two acylases and their genes, respectively.

EXAMPLE 3

Purification of the cephalosporin C acylase of Pseudomonas diminuta N-176 from E. coli transformant An aqueous medium (3LB) (400 ml) containing 3% peptone (Difco Laboratories, U.S.A.), 1.5% yeast extract (Difco) and 0.5% NaCl was introduced into each of five 1 l flasks, sterilized at 121° C. for 20 min, and supplemented with 20 $\mu$g/ml kanamycin sulfate (Meiji Seika Co., Ltd., Japan) sterilized separately by filtration. To these media was inoculated a loopful of slant culture of E. coli JM109 possessing pCCN176-2, respectively and the organism was grown at 30° C. for 24 hours with shaking at 300 rpm on a rotary shaker. Meanwhile, an aqueous medium (120 l) comprising the same ingredients as mentioned above plus 0.2% fructose and 0.04 % adecanol (Asahi Denka Co., Ltd., Japan) was introduced into a 150 l jar fermenter, sterilized at 121° C. for 15 min and supplemented with 0.25 mg/ml IPTG sterilized separately by filtration. To the medium was inoculated whole volume of the cultured broth as obtained above, whereafter the organism was grown at 28° C. The fermentation was conducted by stirring the broth with a propeller equipment at 250 rpm and passing sterile air through the broth at a rate of one volume per volume of broth per minute. After 20 hours of cultivation, 10 g of IPTG and 1 kg of yeast extract, both of which were sterilized, were added to the culture broth and the organism was further grown for 2.5 hours. After the completion of the culture, the jar fermenter was cooled to 5° C. and the cells were harvested by continuous flow centrifugation at 20,000 rpm using a sharpless centrifuge. The cell pellet (approximately 2 kg) obtained was suspended in 20 mM Tris-HCl buffer (pH 8) at concentration of 100 g (wet weight) per l. To this Ltd.) were added to make final concentrations of 40 u/ml, 12.5 $\mu$g/ml and 1 mg/ml, respectively, and the mixture was incubated at room temperature for 2 hours with stirring. After incubation, the suspension was centrifuged at 10,000 g for 40 min and the resulting supernatant was dialyzed overnight against water. Meanwhile, the pellet was resuspended in 20 mM Tris-HCl buffer (pH 8) and disrupted in an ice-water bath by four pulses of 30 sec of sonication. The sonicated suspension was centrifuged at 10,000 g for 60 min and the resulting supernatant was also dialyzed overnight against water. Two dialyzed solutions were combined and subjected to another centrifugation at 10,000 g for 40 min. The resulting supernatant was used as crude extract. The crude extract was applied onto a column of DEAE-Toyopearl 650H (Toso Co., Ltd., Japan) (15×15 cm) which had been equilibrated with 20 mM Tris HCl buffer (pH 8). After Washing the column with the same buffer, the column was eluted with 20 mM Tris-HCl buffer (pH 8) containing 100 mM NaCl. Fractions containing cephalosporin C acylase activity were pooled and adjusted to 60% saturation with ammonium sulfate, stirred for 30 min and centrifuged at 10,000 g for 20 min. The resulting pellet was dissolved in 20 mM phosphate buffer pH 7), adjusted to 35% saturation with ammonium sulfate and applied onto a column of Toyopearl HW55F (Toso)(9.5×10 cm) equilibrated with the same buffer containing ammonium sulfate of 35% saturation.

After washing with the same buffer, the column was eluted with 20 mM phosphate buffer (pH 7) containing ammonium sulfate of 20% saturation. Fractions containing cephalosporin C acylase activity were pooled, adjusted to 60% saturation with ammonium sulfate, stirred for 30 min and centrifuged at 10,000 g for 20 min. The resulting pellet was dissolved in 20 mM phosphate buffer (pH 7), adjusted to 15% saturation with ammonium sulfate and applied onto an HPLC column of Butyl-Toyopearl 650s (Toso, 2.2 cm×20.0 cm) equilibrated with the same buffer containing ammonium sulfate of 15% saturation. Elution was performed with a linear gradient of ammonium sulfate (15–0% saturation) in 100 mM phosphate buffer (pH 8) at a flow rate of 4 ml/min over 120 min. Fractions containing cephalosporin C acylase activity were pooled, adjusted to 60% saturation with ammonium sulfate, stirred for 30 min and centrifuged at 10,000 g for 30 min. The pellet was dissolved in 20 mM Tris-HCl buffer (pH 8) and dialyzed against the same buffer. The dialysate was applied onto an HPLC column of TSK gel DEAE-Toyopearl 5PW (Toso, 2.15 cm×15 cm) equilibrated with 20 mM Tris-HCl buffer (pH 8) and elution was performed with a linear gradient of NaCl (0–250 mM) in 20 mM Tris-HCl buffer (pH 8) at a flow rate of 5 ml/min over 180 min. Fractions containing cephalosporin C acylase activity were pooled, dialyzed against 20 mM Tris-HCl buffer (pH 8) and applied again onto an HPLC column of TSK gel DEAE-Toyopearl 5PW (Toso, 0.75×7.5 cm). Elution was performed with a linear gradient of NaCl (0–250 mM) in 20 mM Tris-HCl buffer (pH 8) at a flow rate of 1 ml/min over 180 min. Fractions containing cephalosporin C acylase activity were pooled, dialyzed against 20 mM Tris-HCl buffer (pH 8) and used as the enzyme preparation. The total quantity of the final enzyme preparation was 10 mg and its purity was estimated to be 95%.

EXAMPLE 4

Characterization of the cephalosporin C acylase of Pseudomonas diminuta N-176 from an E. coli transformant

4.1. Specific enzyme activity

The activity of the cephalosporin C acylase was determined by HPLC assay. Reaction mixtures (200 μl) containing 100 mM glycine buffer (pH 9), 1.25–40 mM Cephalosporin C Li and 19 μg of the enzyme is used for assay of cephalosporin C acylase, meanwhile for assay of GL-7ACA acylase activity, reaction mixture (200 μl) containing 100 mM glycine buffer (pH 9), 0.48–10.4 mM GL-7ACA and 0.5 μg of the enzyme is used. Reaction mixtures were incubated for 2 min at 37° C. and the reaction was terminated by addition of 200 μl of 4% acetic acid. Conditions for HPLC were the same as those described in Example 1.3. All assays used later in this section was HPLC method. Specific enzyme activity was expressed as unit per mg of protein. Protein concentrations were determined by Bio-Rad protein assay kit (Bio-Rad Co., Ltd., U.S.A.) with bovine serum albumin as a standard. Maximum specific enzyme activity (Vmax) and Michaelis constant (Km) were calculated from slope and intersection which were obtained by Lineweaver-Burk plot (Cf. M. Dixon and E. C. Webb, Enzymes, Longmans, London, 1958). Maximum specific enzyme activity of CC acylase N-176 was 100 and 3.1 units/mg for GL-7ACA and cephalosporin C, respectively. Km values of CC acylase N-176 was 2.6 and 4.8 mM for GL-7ACA and cephalosporin C.

4.2. Substrate profile

Enzyme activity was determined by HPLC assay. Reaction mixture (200 μl) containing 100 mM glycine buffer (pH 9), 2 mg of a substrate and 20 μg of the enzyme was incubated at 50° C. for 2 min and the reaction was terminated by addition of 4% acetic acid. The relative enzyme activity was expressed as a percentage compared to the activity for GL-7ACA. To be noted, acylase activity for cephalosporin C was examined also by detecting the production of a-aminoadipic acid with the amino acid analyzer (Hitachi Co., Ltd., Japan).

TABLE 3

| Substrate profile of CC acyalse N-176 | |
|---|---|
| Substrates | Relative enzyme activity |
| Succinyl 7ACA | 32 |
| Glutaryl 7ACA | 100 |
| Adipyl 7ACA | 19 |
| Cephalosporin C | 4 |
| N-Acetylcephalosporin C | 0.1 |
| N-Benzoylcephalosporin C | 0.0003 |
| Cephalothin | 0.08 |

Note)
Succinyl 7ACA: 7-(3-carboxypropionamido)-3-acetoxymethyl-3-cephem-4-carboxylic acid
Glutaryl 7ACA: 7-(4-carboxybutanamido)-3-acetoxymethyl-3-cephem-4-carboxylic acid
Adipyl 7ACA: 7-(5-carboxypentanamido)-3-acetoxymethyl-3-cephem-4-carboxylic acid

Figure 3:
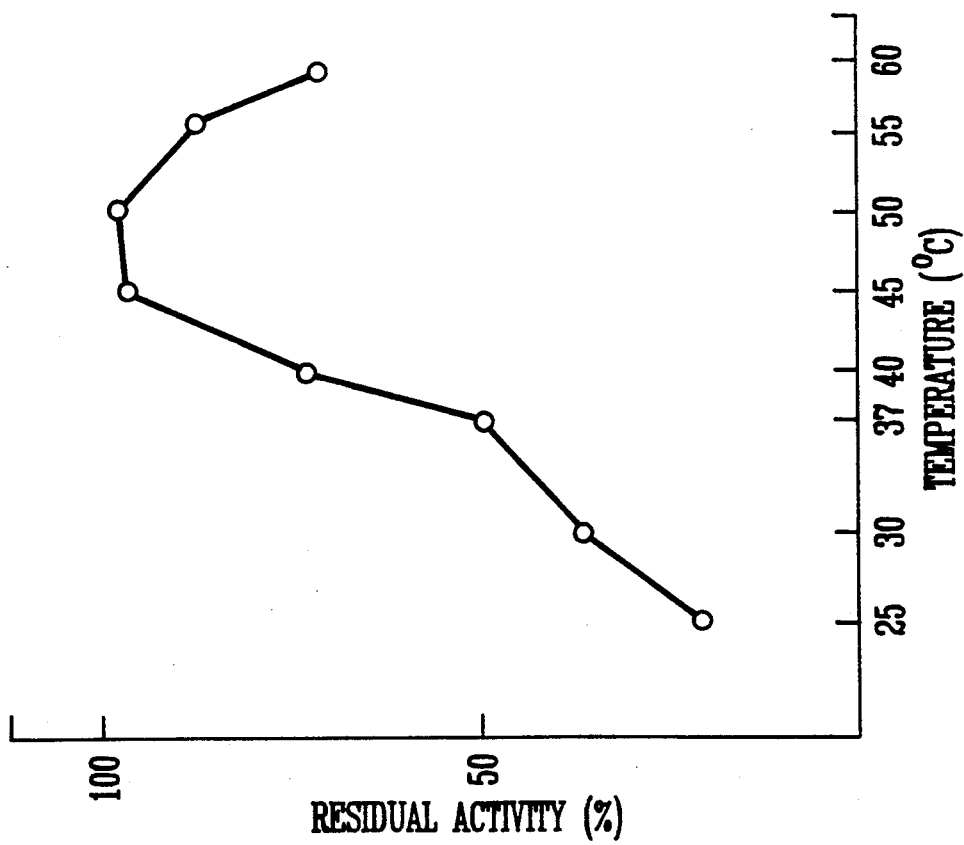
FIG. 3 shows optimum temperature of the CC acylase N-176.

4.3. Effect of temperature (Cf. FIG. 3)

a) Optimum temperature

Figure 4:
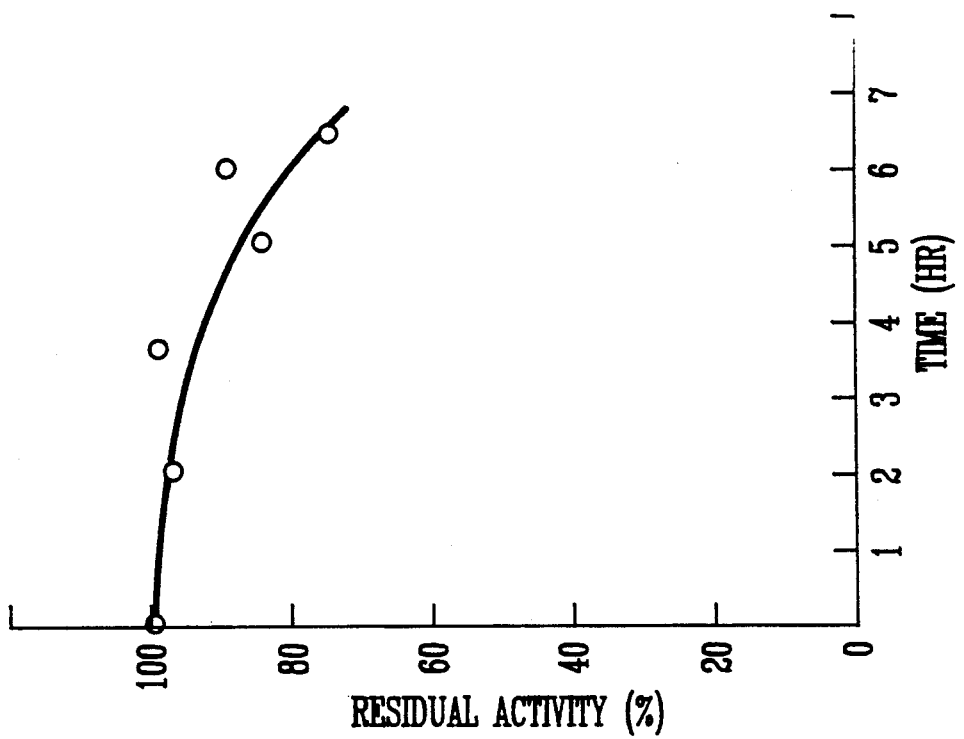
FIG. 4 shows thermostability of the CC acylase N-176.

Reaction mixture (200 μl) containing 0.1M glycine buffer (pH 9), 2 mg of GL-7ACA and 2 μg of the enzyme were incubated for 2 min at various temperature from 25° to 60° C. The optimum temperature was 50° C.

b) Thermostability (Cf. FIG. 4)

One hundred μg/ml of the enzyme was treated in 0.1 M glycine buffer (pH 9) at 50° C. for 6.5 hours. Aliquotes of the treated enzyme were sampled at 2, 3.5, 5, 6 and 6.5 hours later and the residual enzyme activities were assayed in the reaction mixture containing 0.1M glycine buffer (pH 9), 10 mg/ml of GL-7ACA and 10 μg/ml of the treated enzyme. The reaction was performed at 37° C. for 2 min.

Figure 5B:
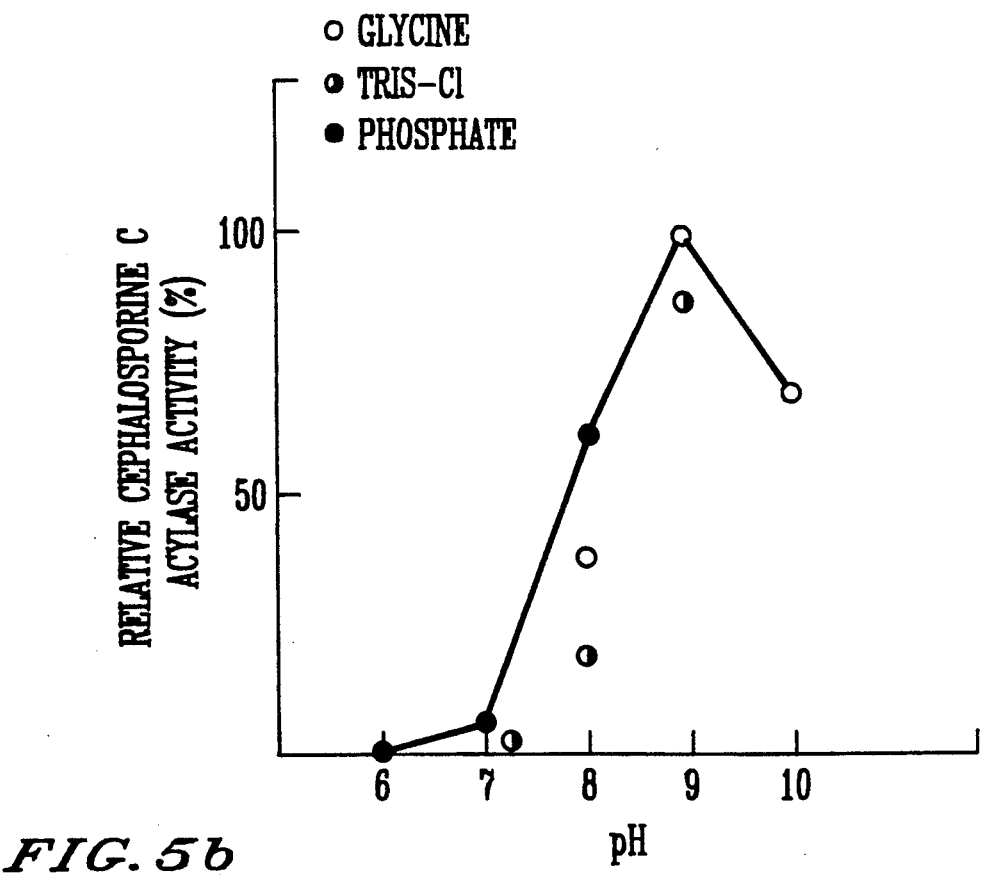

4.4. Effect of pH (Cf. FIG. 5)

a) Optimum pH

Reaction mixture (200 μl) containing 0.1M buffer (phosphate buffer between pH 6–8, Tris HCl buffer between pH 7–9 and glycine buffer between pH 8–10), 2 mg of GL-7ACA or 3.3 mg of cephalosporin C Li and 3 μg of the enzyme was used. The reaction was performed at 37° C. for 2 min. Optimum pH for the enzyme was 9.

b) pH profile of stability (Cf. FIG. 6)

One hundred μg/ml of the enzyme was treated at 50° C. for 1 hour in 0.1M buffer of various pH (phosphate buffer used for pH 6 and 7 and glycine buffer for pH 8, 9 and 10). The residual enzyme activity was assayed in the reaction mixture (200 μl) containing 0.1M glycine buffer (pH 9), 2 mg of GL-7ACA and 2 μg of the treated enzyme. Reaction was performed at 37° C. for 2 min.

Figure 7B:
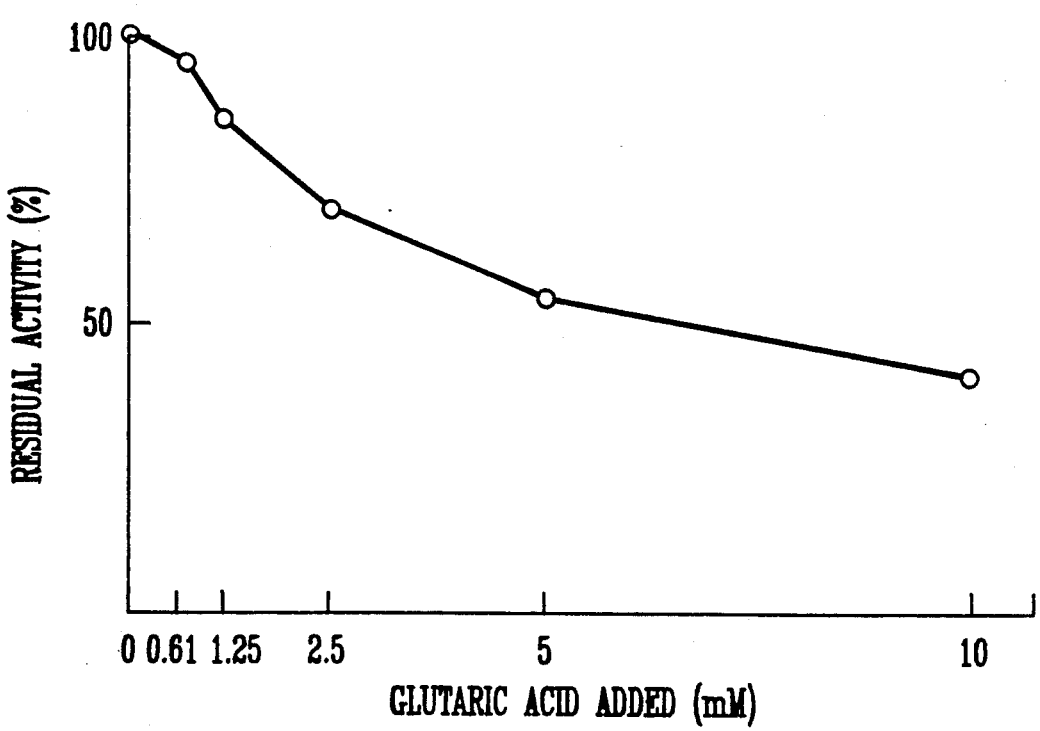
Figure 8B:
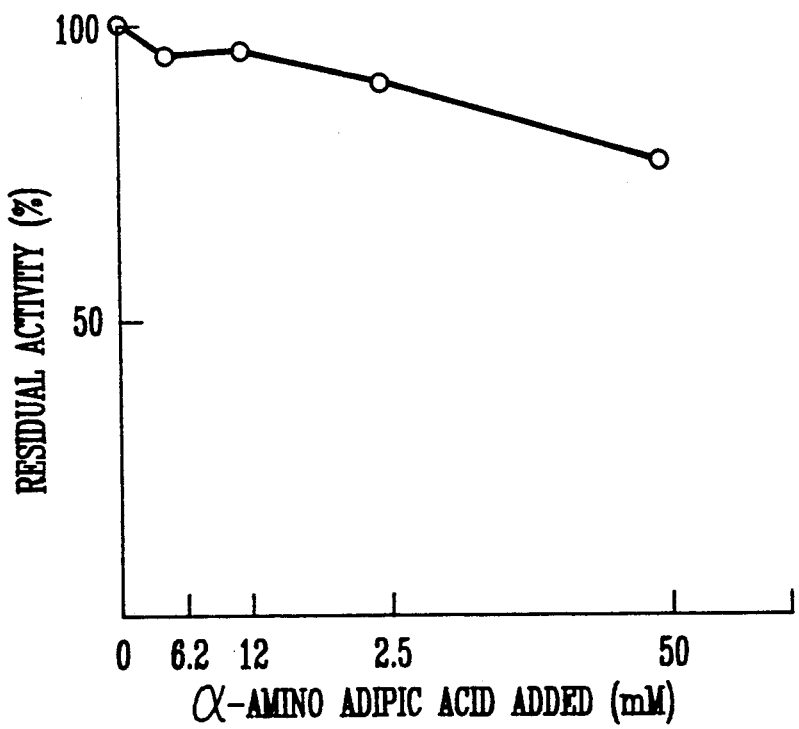

4.5. Inhibition by reaction products (Cf. FIG. 7 and FIG. 8)

a) Effect of reaction products on the enzyme activity of the enzyme

Inhibitory activity of reaction products, namely 7-ACA, α-aminoadipic acid and glutaric acid on the enzyme activity of the enzyme was examined. The enzyme activity was assayed in the presence of various concentrations of 7-ACA, α-aminoadipic acid or glutaric acid. Reaction mixture (200 μl) containing besides the reaction product, 0.1M glycine buffer [pH 9), 2 mg of cephalosporin C Li and 200 μg of the enzyme is used for cephalosporin C acylase activity and reaction mixture containing 0.1M glycine buffer (pH 9), 200 μg of GL-7ACA and 5 μg of the enzyme is used for GL-7ACA acylase activity. The reaction was performed at 40° C. for 5 min for cephalosporin C acylase activity or at 37° C. for 1 min for GL-7ACA acylase activity.

b) Determination of inhibition constants (Ki) for reaction products

Enzyme activity was assayed in the presence of 7-ACA or glutaric acid. For determination of Ki of 7-ACA, reaction mixtures (200 μl) containing 0.1M glycine buffer (pH 9), 0.26-2.08 μmole of GL-7ACA, 0.182-1.0 μmole of 7-ACA and 1 μg of enzyme was incubated at 37° C. for 3 min. For determination of Ki of glutaric acid, reaction mixture (200 μl) containing 0.1M glycine buffer (pH 9), 0.096-2.08 μmole of GL-7ACA, 0.25-0.5 μmole of glutaric acid and 0.5 μg of the enzyme was incubated at 37° C. for 3 min. Line-weaver Burk plots in the absence and presence of either incubator were shown to possess the same intersection at vertical axis, indication the mode of inhibition by either inhibitor was competitive. Ki values were calculated from the apparent Michaelis constants (Kmapp), Km and Vmax. Ki values of 7-ACA and glutaric acid were 1.4 and 2.5 mM, respectively.

c) Effect of various enzyme inhibitors

Effect of p-chloromercuribenzoate (pCMB, Sigma Chemical Co., Ltd.), phenylmethylsulfonyl fluoride (PMSF, Sigma) and ethylenediaminetetraacetic acid (EDTA, Nacalai Tesque Inc., Japan) on the activity of CC acylase N-176 was examined as follows. Four μg of CC acylase N-176 was treated at 37° C. for 4 hours with 0. 1or 1.0 mM pCMB, 0.1, 1.0, 2.0 or 5.0 mM PMSF, or 1.0 or 5.0 mM EDTA in 200 μl of 0.1M glycine buffer (pH 9). Residual activity of the treated enzyme was assayed by adding 22 μl of GL-7ACA (100 mg/ml) as a substrate to the mixture. The reaction was performed at 37° C. for 2 min. Residual activity was expressed as a percentage compared to the activity of the enzyme treated with blank solution.

TABLE 4

Effect of enzyme inhibitors on the activity of CC acylase N-176

| Inhibitors | Concentration (mM) | Residual enzyme activity (%) |
|---|---|---|
| pCMB | 0.1 | 7.8 |
|  | 1.0 | 4.6 |
| PMSF | 0.1 | 96 |
|  | 1.0 | 91 |
|  | 2.0 | 79 |
|  | 5.0 | 62 |
| EDTA | 1.0 | 91 |
|  | 5.0 | 73 |

4.6 Determination of isoelectric point (pI)

Analytical isoelectric focusing of CC acylase N-176 was performed according to the method of Olson et al(Cf.FEMS Microbiol.Lett.1, 157-162(1977)). Purified acylase preparation was applied on thin layer of 4% polyacrylamide gel containing 2% Ampholine pH range 3.5-10 (Pharmacia LKB Biotechnology, Sweden). The proteins were electrofocused for 2 hours at 100 volts using isoelectric focusing apparatus SJ-1071EC (ATTO Co., Ltd., Japan). After electrofocusing, the gel was stained with Coomassie Brilliant Blue R-250 and the isoelectric point was determined from the calibration curve made with pI markers (Pharmacia LKB Technology) which were run simultaneously with the sample. The pI value of CC analyse N-176 was estimated to be 4.5.

4.7 Determination of molecular weight by SDS-polyacrylamide gel electrophoresis Sodium dodecyl sulfate (SDS)-polyacrylamide gel electrophoresis was performed by the procedure described by Laemmli (Cf. U. K. Laemmli; Nature 237, 680-685 (1970)). Egg white lysozyme (molecular weight 14,000), soybean trypsin inhibitor (21,000), bovine carbonic anhydrase (31,000), egg white ovalbumin (43,000), bovine serum albumin (68,000), rabbit muscle phosphorylase b (97,000) were purchased from BioRad Laboratories and used as molecular weight standards. The final preparation of CC acylase N-176 purified as described in Example 3 showed two discrete bands on SDS-gel electrophoresis, whose intensities were proportional to be corresponding molecular weights. The molecular weights of the two proteins calculated from their mobility on gel electrophoresis were 26,000 and 58,000. CC acylase N-176 was concluded to be composed of two heterologous subunits (α and β) of molecular weights 26,000 (α) and 58,000 (β).

4.8. Determination of amino acid sequence

CC acylase N-176 is composed of two heterologous subunits α and β as described in Example 4.7. Each subunit was isolated by reversed phase HPLC. Column used was Cosmosil 5C4-300 (4.6 mm×5 cm, Nacalai tesque). Elution was performed with a linear gradient of acetonitrile (30% to 60%) in 0.1% trifluoroacetic acid at a flow rate of 1 ml/min over 20 min. The amino acid sequence of each subunit purified as above was determined by a gas-phase sequencer 470A (Applied Biosystems, U.S.A.). The N-terminal amino acid sequences of α and β subunits were Thr-Met-Ala-Ala-Asn-Thr-Asp-Arg-Ala-Val-Leu-Gln-Ala-Ala-Leu-Pro-Pro-Leu (SEQ ID NO:1) and Ser-Asn-Asn-Trp-Ala-Val-Ala-Pro-Gly-Arg-Thr-Ala-Thr-Gly-Arg (SEQ ID NO:4), respectively.

The expression plasmid, pCCN176-2 obtained in the above Example was inserted into *Escherichia coli* JM109 and the resultant transformant as mentioned below has been deposited with one of the INTERNATIONAL DEPOSITORY AUTHORITY ON THE BUDAPEST TREATY, Fermentation Research Institute(-FRI), Agency of Industrial Science and Technology at 1-3, Higashi 1 chome, Tsukubashi, Ibaraki-ken 305, Japan on Aug. 7, 1990.

| Organism | Deposit number |
|---|---|
| *Escheichia coli* JM109 (pCCN176-2) | FERM BP-3047 |

5

We claim:

1. An isolated and purified cephalosporin C acylase having the following characteristics:
   (a) has ability to catalyze the enzymatic conversion of cephalosporin C, glutaryl 7-ACA, adipyl 7-ACA, succinyl 7-ACA, N-acetylcephalosporin C, N-benzoylcephalosporin C and cephalothin into 7-amino cephalosporanic acid,
   (b) is composed of an α-subunit with a molecular weight of 26,000 daltons as measured by SDS-PAGE and a β-subunit with a molecular weight of 58,000 daltons as measured by SDS-PAGE,
   (c) has N-terminal amino acid sequence of the α-subunit: Thr-Met-Ala-Ala-Asn-Thr-Asp-Arg-Ala-Val-Leu-Gln-Ala-Ala-Leu-Pro-Pro-Leu- (SEQ ID NO:1).

2. A cephalosporin C acylase of claim 1 which comprises the amino acid sequence (SEQ ID NO:3) represented in FIG. 2.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

```
Thr Met Ala Ala Asn Thr Asp Arg Ala Val Leu Gln Ala Ala Leu Pro
 1               5                  10                  15

Pro Leu
```

( 2 ) INFORMATION FOR SEQ ID NO:2:

( i ) SEQUENCE CHARACTERISTICS:
        ( A ) LENGTH: 2847 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 483..2804

( x i ) SEQUENCE DESCRIPTION: SEQ ID NO:2:

```
CCCGGGGATC TCGCAGACGG CTGGCGCGGT CCTGGCCAGC AATATGCGCA AGGCCGGCTT        60

CACGGTGGAA GAGCAGGTGA TGGATTGGGG CACGGTGCTC GCCCGCCGGG CCAAGAAGGA       120

CGGCTGGAGC GTTTTCCCGG TCTACGCCAA CGGCATCGAC ATGATGTCGC CGCTGACGCA       180

TTTCTACATC GGCAACAACT GCGTGAACTA TGCGGGCTGG AGCTGCGACG CCGTCATCAC       240

CGAAAAGCTC GCCGCCTATG CCAAGGCGCC CGATCCGGCT ACCCGCAAAC GCATCGCGGC       300

CGAAATCCAG GTCGAGGCCT ACAAGGACAC GCCCTCCGTG ATGTGGGGCC AGTTCAGCCG       360

GCCGGCGGGC TACCGCCTGC GCCTCAAGAA CATCGTCCAG TCCAGCTTCC CGATCTTCTG       420

GCAGCTCACG CTCGACGCGT GAGCTTGCCC AGATTCCGAC AAGCAATGAG GTCCCGACGC       480

GA ATG ACT ATG GCG GCC AAC ACC GAT CGC GCG GTC TTG CAG GCG GCG          527
   Met Thr Met Ala Ala Asn Thr Asp Arg Ala Val Leu Gln Ala Ala
    1               5                  10                  15

CTG CCG CCG CTT TCC GGC AGC CTC CCC ATT CCC GGA TTG AGC GCG TCG        575
Leu Pro Pro Leu Ser Gly Ser Leu Pro Ile Pro Gly Leu Ser Ala Ser
                  20                  25                  30

GTC CGC GTC CGG CGC GAT GCC TGG GGC ATC CCG CAT ATC AAG GCC TCG        623
Val Arg Val Arg Arg Asp Ala Trp Gly Ile Pro His Ile Lys Ala Ser
              35                  40                  45

GGC GAG GCC GAT GCC TAT CGG GCG CTG GGC TTC GTC CAT TCG CAG GAC        671
```

-continued

| | | | | | | | | | | | | | | | | |
|---|---|---|---|---|---|---|---|---|---|---|---|---|---|---|---|---|
| Gly | Glu | Ala | Asp | Ala | Tyr | Arg | Ala | Leu | Gly | Phe | Val | His | Ser | Gln | Asp | |
| | | 50 | | | | 55 | | | | | | 60 | | | | |

| CGT | CTT | TTC | CAG | ATG | GAG | CTG | ACG | CGT | CGC | AAG | GCG | CTG | GGA | CGC | GCG | 719 |
|---|---|---|---|---|---|---|---|---|---|---|---|---|---|---|---|---|
| Arg | Leu | Phe | Gln | Met | Glu | Leu | Thr | Arg | Arg | Lys | Ala | Leu | Gly | Arg | Ala | |
| | 65 | | | | 70 | | | | | 75 | | | | | | |

| GCC | GAA | TGG | CTG | GGC | GCC | GAG | GCC | GCC | GAG | GCC | GAT | ATC | CTC | GTG | CGC | 767 |
|---|---|---|---|---|---|---|---|---|---|---|---|---|---|---|---|---|
| Ala | Glu | Trp | Leu | Gly | Ala | Glu | Ala | Ala | Glu | Ala | Asp | Ile | Leu | Val | Arg | |
| 80 | | | | | 85 | | | | | 90 | | | | | 95 | |

| CGG | CTC | GGA | ATG | GAA | AAA | GTC | TGC | CGG | CGC | GAC | TTC | GAG | GCC | TTG | GGC | 815 |
|---|---|---|---|---|---|---|---|---|---|---|---|---|---|---|---|---|
| Arg | Leu | Gly | Met | Glu | Lys | Val | Cys | Arg | Arg | Asp | Phe | Glu | Ala | Leu | Gly | |
| | | | | 100 | | | | | 105 | | | | | 110 | | |

| GTC | GAG | GCG | AAG | GAC | ATG | CTG | CGG | GCT | TAT | GTC | GCC | GGC | GTG | AAC | GCA | 863 |
|---|---|---|---|---|---|---|---|---|---|---|---|---|---|---|---|---|
| Val | Glu | Ala | Lys | Asp | Met | Leu | Arg | Ala | Tyr | Val | Ala | Gly | Val | Asn | Ala | |
| | | | 115 | | | | 120 | | | | | 125 | | | | |

| TTC | CTG | GCT | TCC | GGT | GCT | CCC | CTG | CCT | GTC | GAA | TAC | GGA | TTG | CTC | GGA | 911 |
|---|---|---|---|---|---|---|---|---|---|---|---|---|---|---|---|---|
| Phe | Leu | Ala | Ser | Gly | Ala | Pro | Leu | Pro | Val | Glu | Tyr | Gly | Leu | Leu | Gly | |
| | 130 | | | | | 135 | | | | | 140 | | | | | |

| GCA | GAG | CCG | GAG | CCC | TGG | GAG | CCT | TGG | CAC | AGC | ATC | GCG | GTG | ATG | CGC | 959 |
|---|---|---|---|---|---|---|---|---|---|---|---|---|---|---|---|---|
| Ala | Glu | Pro | Glu | Pro | Trp | Glu | Pro | Trp | His | Ser | Ile | Ala | Val | Met | Arg | |
| 145 | | | | | 150 | | | | | 155 | | | | | | |

| CGG | CTG | GGC | CTG | CTT | ATG | GGT | TCG | GTG | TGG | TTC | AAG | CTC | TGG | CGG | ATG | 1007 |
|---|---|---|---|---|---|---|---|---|---|---|---|---|---|---|---|---|
| Arg | Leu | Gly | Leu | Leu | Met | Gly | Ser | Val | Trp | Phe | Lys | Leu | Trp | Arg | Met | |
| 160 | | | | | 165 | | | | | 170 | | | | | 175 | |

| CTG | GCG | CTG | CCG | GTG | GTC | GGA | GCC | GCG | AAT | GCG | CTG | AAG | CTG | CGC | TAT | 1055 |
|---|---|---|---|---|---|---|---|---|---|---|---|---|---|---|---|---|
| Leu | Ala | Leu | Pro | Val | Val | Gly | Ala | Ala | Asn | Ala | Leu | Lys | Leu | Arg | Tyr | |
| | | | | 180 | | | | | 185 | | | | | 190 | | |

| GAC | GAT | GGC | GGC | CGG | GAT | TTG | CTC | TGC | ATC | CCG | CCG | GGC | GCC | GAA | GCC | 1103 |
|---|---|---|---|---|---|---|---|---|---|---|---|---|---|---|---|---|
| Asp | Asp | Gly | Gly | Arg | Asp | Leu | Leu | Cys | Ile | Pro | Pro | Gly | Ala | Glu | Ala | |
| | | | 195 | | | | 200 | | | | | 205 | | | | |

| GAT | CGG | CTC | GAG | GCG | GAT | CTC | GCG | ACC | CTG | CGG | CCC | GCG | GTC | GAT | GCG | 1151 |
|---|---|---|---|---|---|---|---|---|---|---|---|---|---|---|---|---|
| Asp | Arg | Leu | Glu | Ala | Asp | Leu | Ala | Thr | Leu | Arg | Pro | Ala | Val | Asp | Ala | |
| | | 210 | | | | | 215 | | | | | 220 | | | | |

| CTG | CTG | AAG | GCG | ATG | GGC | GGC | GAT | GCC | TCC | GAT | GCT | GCC | GGC | GGC | GGC | 1199 |
|---|---|---|---|---|---|---|---|---|---|---|---|---|---|---|---|---|
| Leu | Leu | Lys | Ala | Met | Gly | Gly | Asp | Ala | Ser | Asp | Ala | Ala | Gly | Gly | Gly | |
| | 225 | | | | | 230 | | | | | 235 | | | | | |

| AGC | AAC | AAC | TGG | GCG | GTC | GCT | CCG | GGC | CGC | ACG | GCG | ACC | GGC | AGG | CCG | 1247 |
|---|---|---|---|---|---|---|---|---|---|---|---|---|---|---|---|---|
| Ser | Asn | Asn | Trp | Ala | Val | Ala | Pro | Gly | Arg | Thr | Ala | Thr | Gly | Arg | Pro | |
| 240 | | | | | 245 | | | | | 250 | | | | | 255 | |

| ATC | CTC | GCG | GGC | GAT | CCG | CAT | CGC | GTC | TTC | GAA | ATC | CCG | GGC | ATG | TAT | 1295 |
|---|---|---|---|---|---|---|---|---|---|---|---|---|---|---|---|---|
| Ile | Leu | Ala | Gly | Asp | Pro | His | Arg | Val | Phe | Glu | Ile | Pro | Gly | Met | Tyr | |
| | | | | 260 | | | | | 265 | | | | | 270 | | |

| GCG | CAG | CAT | CAT | CTG | GCC | TGC | GAC | CGG | TTC | GAC | ATG | ATC | GGC | CTG | ACC | 1343 |
|---|---|---|---|---|---|---|---|---|---|---|---|---|---|---|---|---|
| Ala | Gln | His | His | Leu | Ala | Cys | Asp | Arg | Phe | Asp | Met | Ile | Gly | Leu | Thr | |
| | | | 275 | | | | | 280 | | | | | 285 | | | |

| GTG | CCG | GGC | GTG | CCG | GGC | TTC | CCG | CAC | TTC | GCG | CAT | AAC | GGC | AAG | GTC | 1391 |
|---|---|---|---|---|---|---|---|---|---|---|---|---|---|---|---|---|
| Val | Pro | Gly | Val | Pro | Gly | Phe | Pro | His | Phe | Ala | His | Asn | Gly | Lys | Val | |
| | | 290 | | | | | 295 | | | | | 300 | | | | |

| GCC | TAT | TGC | GTC | ACC | CAT | GCC | TTC | ATG | GAC | ATC | CAC | GAT | CTC | TAT | CTC | 1439 |
|---|---|---|---|---|---|---|---|---|---|---|---|---|---|---|---|---|
| Ala | Tyr | Cys | Val | Thr | His | Ala | Phe | Met | Asp | Ile | His | Asp | Leu | Tyr | Leu | |
| | 305 | | | | | 310 | | | | | 315 | | | | | |

| GAG | CAG | TTC | GCG | GGG | GAG | GGC | CGC | ACT | GCG | CGG | TTC | GGC | AAC | GAT | TTC | 1487 |
|---|---|---|---|---|---|---|---|---|---|---|---|---|---|---|---|---|
| Glu | Gln | Phe | Ala | Gly | Glu | Gly | Arg | Thr | Ala | Arg | Phe | Gly | Asn | Asp | Phe | |
| 320 | | | | | 325 | | | | | 330 | | | | | 335 | |

| GAG | CCC | GTC | GCC | TGG | AGC | CGG | GAC | CGT | ATC | GCG | GTC | CGG | GGT | GGC | GCC | 1535 |
|---|---|---|---|---|---|---|---|---|---|---|---|---|---|---|---|---|
| Glu | Pro | Val | Ala | Trp | Ser | Arg | Asp | Arg | Ile | Ala | Val | Arg | Gly | Gly | Ala | |
| | | | | 340 | | | | | 345 | | | | | 350 | | |

| GAT | CGC | GAG | TTC | GAT | ATC | GTC | GAG | ACG | CGC | CAT | GGC | CCG | GTT | ATC | GCG | 1583 |
|---|---|---|---|---|---|---|---|---|---|---|---|---|---|---|---|---|
| Asp | Arg | Glu | Phe | Asp | Ile | Val | Glu | Thr | Arg | His | Gly | Pro | Val | Ile | Ala | |
| | | | 355 | | | | | 360 | | | | | 365 | | | |

| GGC | GAT | CCG | CGC | GAT | GGC | GCA | GCG | CTC | ACG | CTG | CGT | TCG | GTC | CAG | TTC | 1631 |
|---|---|---|---|---|---|---|---|---|---|---|---|---|---|---|---|---|
| Gly | Asp | Pro | Arg | Asp | Gly | Ala | Ala | Leu | Thr | Leu | Arg | Ser | Val | Gln | Phe | |
| | | 370 | | | | | 375 | | | | | 380 | | | | |

```
GCC GAG ACC GAT CTG TCC TTC GAC TGC CTG ACG CGG ATG CCG GGC GCA      1679
Ala Glu Thr Asp Leu Ser Phe Asp Cys Leu Thr Arg Met Pro Gly Ala
    385                 390                 395

TCG ACC GTG GCC CAG CTC TAC GAC GCG ACG CGC GGC TGG GGC CTG ATC      1727
Ser Thr Val Ala Gln Leu Tyr Asp Ala Thr Arg Gly Trp Gly Leu Ile
400                 405                 410                 415

GAC CAT AAC CTC GTC GCC GGG GAT GTC GCG GGC TCG ATC GGC CAT CTG      1775
Asp His Asn Leu Val Ala Gly Asp Val Ala Gly Ser Ile Gly His Leu
                420                 425                 430

GTC CGC GCC CGC GTT CCG TCC CGT CCG CGC GAA AAC GGC TGG CTG CCG      1823
Val Arg Ala Arg Val Pro Ser Arg Pro Arg Glu Asn Gly Trp Leu Pro
            435                 440                 445

GTG CCG GGC TGG TCC GGC GAG CAT GAA TGG CGG GGC TGG ATT CCG CAC      1871
Val Pro Gly Trp Ser Gly Glu His Glu Trp Arg Gly Trp Ile Pro His
        450                 455                 460

GAG GCG ATG CCG CGC GTG ATC GAT CCG CCG GGC GGC ATC ATC GTC ACG      1919
Glu Ala Met Pro Arg Val Ile Asp Pro Pro Gly Gly Ile Ile Val Thr
    465                 470                 475

GCG AAT AAT CGC GTC GTG GCC GAT GAC CAT CCC GAT TAT CTC TGC ACC      1967
Ala Asn Asn Arg Val Val Ala Asp Asp His Pro Asp Tyr Leu Cys Thr
480                 485                 490                 495

GAT TGC CAT CCG CCC TAC CGC GCC GAG CGC ATC ATG AAG CGC CTG GTC      2015
Asp Cys His Pro Pro Tyr Arg Ala Glu Arg Ile Met Lys Arg Leu Val
                500                 505                 510

GCC AAT CCG GCT TTC GCC GTC GAC GAT GCC GCC GCG ATC CAT GCC GAT      2063
Ala Asn Pro Ala Phe Ala Val Asp Asp Ala Ala Ala Ile His Ala Asp
            515                 520                 525

ACG CTG TCG CCC CAT GTC GGG TTG CTG CGC CGG AGG CTC GAG GCG CTT      2111
Thr Leu Ser Pro His Val Gly Leu Leu Arg Arg Arg Leu Glu Ala Leu
        530                 535                 540

GGA GCC CGC GAC GAC TCC GCG GCC GAA GGG CTG AGG CAG ATG CTC GTC      2159
Gly Ala Arg Asp Asp Ser Ala Ala Glu Gly Leu Arg Gln Met Leu Val
    545                 550                 555

GCC TGG GAC GGC CGC ATG GAT GCG GCT TCG GAG GTC GCG TCT GCC TAC      2207
Ala Trp Asp Gly Arg Met Asp Ala Ala Ser Glu Val Ala Ser Ala Tyr
560                 565                 570                 575

AAT GCG TTC CGC AGG GCG CTG ACG CGG CTG GTG ACG GAC CGC AGC GGG      2255
Asn Ala Phe Arg Arg Ala Leu Thr Arg Leu Val Thr Asp Arg Ser Gly
                580                 585                 590

CTG GAG CAG GCG ATA TCG CAT CCC TTC GCG GCT GTC GCG CCG GGC GTC      2303
Leu Glu Gln Ala Ile Ser His Pro Phe Ala Ala Val Ala Pro Gly Val
            595                 600                 605

TCA CCG CAA GGC CAG GTC TGG TGG GCC GTG CCG ACC CTG CTG CGC GAC      2351
Ser Pro Gln Gly Gln Val Trp Trp Ala Val Pro Thr Leu Leu Arg Asp
        610                 615                 620

GAC GAT GCC GGA ATG CTG AAG GGC TGG AGC TGG GAC CAG GCC TTG TCT      2399
Asp Asp Ala Gly Met Leu Lys Gly Trp Ser Trp Asp Gln Ala Leu Ser
    625                 630                 635

GAG GCC CTC TCG GTC GCG TCG CAG AAC CTG ACC GGG CGA AGC TGG GGC      2447
Glu Ala Leu Ser Val Ala Ser Gln Asn Leu Thr Gly Arg Ser Trp Gly
640                 645                 650                 655

GAA GAG CAT CGG CCG CGC TTC ACG CAT CCG CTT GCC ACG CAA TTC CCG      2495
Glu Glu His Arg Pro Arg Phe Thr His Pro Leu Ala Thr Gln Phe Pro
                660                 665                 670

GCC TGG GCG GGG CTG CTG AAT CCG GCT TCC CGT CCG ATC GGT GGC GAT      2543
Ala Trp Ala Gly Leu Leu Asn Pro Ala Ser Arg Pro Ile Gly Gly Asp
            675                 680                 685

GGC GAT ACC GTG CTG GCG AAC GGG CTC GTC CCG TCA GCC GGG CCG CAG      2591
Gly Asp Thr Val Leu Ala Asn Gly Leu Val Pro Ser Ala Gly Pro Gln
        690                 695                 700

GCG ACC TAT GGT GCC CTG TCG CGC TAC GTC TTC GAT GTC GGC AAT TGG      2639
```

|   |   |   |   |   |   |   |   |   |   |   |   |   |   |   |   |   |
|---|---|---|---|---|---|---|---|---|---|---|---|---|---|---|---|---|
| Ala | Thr | Tyr | Gly | Ala | Leu | Ser | Arg | Tyr | Val | Phe | Asp | Val | Gly | Asn | Trp | |
|  | 705 |  |  |  |  | 710 |  |  |  |  | 715 |  |  |  |  | |
| GAC | AAT | AGC | CGC | TGG | GTC | GTC | TTC | CAC | GGC | GCC | TCC | GGG | CAT | CCG | GCC | 2687 |
| Asp | Asn | Ser | Arg | Trp | Val | Val | Phe | His | Gly | Ala | Ser | Gly | His | Pro | Ala | |
| 720 |  |  |  |  | 725 |  |  |  |  | 730 |  |  |  |  | 735 | |
| AGC | GCC | CAT | TAT | GCC | GAT | CAG | AAT | GCG | CCC | TGG | AGC | GAC | TGT | GCG | ATG | 2735 |
| Ser | Ala | His | Tyr | Ala | Asp | Gln | Asn | Ala | Pro | Trp | Ser | Asp | Cys | Ala | Met | |
|  |  |  |  | 740 |  |  |  |  | 745 |  |  |  |  | 750 |  | |
| GTG | CCG | ATG | CTC | TAT | AGC | TGG | GAC | AGG | ATC | GCG | GCA | GAG | GCC | GTG | ACG | 2783 |
| Val | Pro | Met | Leu | Tyr | Ser | Trp | Asp | Arg | Ile | Ala | Ala | Glu | Ala | Val | Thr | |
|  |  |  | 755 |  |  |  |  | 760 |  |  |  |  | 765 |  |  | |
| TCG | CAG | GAA | CTC | GTC | CCG | GCC | TGAGGGCCGG | GCCTGTTGTC | AGCCTGCCGC |  |  |  |  |  |  | 2834 |
| Ser | Gln | Glu | Leu | Val | Pro | Ala |  |  |  |  |  |  |  |  |  | |
|  |  | 770 |  |  |  |  |  |  |  |  |  |  |  |  |  | |

AGCTCTCTTC GGC 2847

( 2 ) INFORMATION FOR SEQ ID NO:3:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

|   |   |   |   |   |   |   |   |   |   |   |   |   |   |   |   |
|---|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| 1 |  |  |  | 5 |  |  |  |  | 10 |  |  |  |  | 15 |  |
| Pro | Pro | Leu | Ser | Gly | Ser | Leu | Pro | Ile | Pro | Gly | Leu | Ser | Ala | Ser | Val |
|  |  |  | 20 |  |  |  |  | 25 |  |  |  |  | 30 |  |  |
| Arg | Val | Arg | Arg | Asp | Ala | Trp | Gly | Ile | Pro | His | Ile | Lys | Ala | Ser | Gly |
|  |  | 35 |  |  |  |  | 40 |  |  |  |  | 45 |  |  |  |
| Glu | Ala | Asp | Ala | Tyr | Arg | Ala | Leu | Gly | Phe | Val | His | Ser | Gln | Asp | Arg |
|  | 50 |  |  |  |  | 55 |  |  |  |  | 60 |  |  |  |  |
| Leu | Phe | Gln | Met | Glu | Leu | Thr | Arg | Arg | Lys | Ala | Leu | Gly | Arg | Ala | Ala |
| 65 |  |  |  |  | 70 |  |  |  |  | 75 |  |  |  |  | 80 |
| Glu | Trp | Leu | Gly | Ala | Glu | Ala | Ala | Glu | Ala | Asp | Ile | Leu | Val | Arg | Arg |
|  |  |  |  | 85 |  |  |  |  | 90 |  |  |  |  | 95 |  |
| Leu | Gly | Met | Glu | Lys | Val | Cys | Arg | Arg | Asp | Phe | Glu | Ala | Leu | Gly | Val |
|  |  |  | 100 |  |  |  |  | 105 |  |  |  |  | 110 |  |  |
| Glu | Ala | Lys | Asp | Met | Leu | Arg | Ala | Tyr | Val | Ala | Gly | Val | Asn | Ala | Phe |
|  |  | 115 |  |  |  |  | 120 |  |  |  |  | 125 |  |  |  |
| Leu | Ala | Ser | Gly | Ala | Pro | Leu | Pro | Val | Glu | Tyr | Gly | Leu | Leu | Gly | Ala |
|  | 130 |  |  |  |  | 135 |  |  |  |  | 140 |  |  |  |  |
| Glu | Pro | Glu | Pro | Trp | Glu | Pro | Trp | His | Ser | Ile | Ala | Val | Met | Arg | Arg |
| 145 |  |  |  |  | 150 |  |  |  |  | 155 |  |  |  |  | 160 |
| Leu | Gly | Leu | Leu | Met | Gly | Ser | Val | Trp | Phe | Lys | Leu | Trp | Arg | Met | Leu |
|  |  |  |  | 165 |  |  |  |  | 170 |  |  |  |  | 175 |  |
| Ala | Leu | Pro | Val | Val | Gly | Ala | Ala | Asn | Ala | Leu | Lys | Leu | Arg | Tyr | Asp |
|  |  |  | 180 |  |  |  |  | 185 |  |  |  |  | 190 |  |  |
| Asp | Gly | Gly | Arg | Asp | Leu | Leu | Cys | Ile | Pro | Pro | Gly | Ala | Glu | Ala | Asp |
|  |  | 195 |  |  |  |  | 200 |  |  |  |  | 205 |  |  |  |
| Arg | Leu | Glu | Ala | Asp | Leu | Ala | Thr | Leu | Arg | Pro | Ala | Val | Asp | Ala | Leu |
|  | 210 |  |  |  |  | 215 |  |  |  |  | 220 |  |  |  |  |
| Leu | Lys | Ala | Met | Gly | Gly | Asp | Ala | Ser | Asp | Ala | Ala | Gly | Gly | Gly | Ser |
| 225 |  |  |  |  | 230 |  |  |  |  | 235 |  |  |  |  | 240 |
| Asn | Asn | Trp | Ala | Val | Ala | Pro | Gly | Arg | Thr | Ala | Thr | Gly | Arg | Pro | Ile |
|  |  |  |  | 245 |  |  |  |  | 250 |  |  |  |  | 255 |  |
| Leu | Ala | Gly | Asp | Pro | His | Arg | Val | Phe | Glu | Ile | Pro | Gly | Met | Tyr | Ala |

-continued

```
                    260                      265                         270
Gln His His Leu Ala Cys Asp Arg Phe Asp Met Ile Gly Leu Thr Val
        275                     280              285
Pro Gly Val Pro Gly Phe Pro His Phe Ala His Asn Gly Lys Val Ala
    290                 295              300
Tyr Cys Val Thr His Ala Phe Met Asp Ile His Asp Leu Tyr Leu Glu
305             310              315                          320
Gln Phe Ala Gly Glu Gly Arg Thr Ala Arg Phe Gly Asn Asp Phe Glu
                325              330                      335
Pro Val Ala Trp Ser Arg Asp Arg Ile Ala Val Arg Gly Gly Ala Asp
            340             345              350
Arg Glu Phe Asp Ile Val Glu Thr Arg His Gly Pro Val Ile Ala Gly
            355             360              365
Asp Pro Arg Asp Gly Ala Ala Leu Thr Leu Arg Ser Val Gln Phe Ala
    370             375              380
Glu Thr Asp Leu Ser Phe Asp Cys Leu Thr Arg Met Pro Gly Ala Ser
385             390              395                      400
Thr Val Ala Gln Leu Tyr Asp Ala Thr Arg Gly Trp Gly Leu Ile Asp
            405             410              415
His Asn Leu Val Ala Gly Asp Val Ala Gly Ser Ile Gly His Leu Val
            420             425              430
Arg Ala Arg Val Pro Ser Arg Pro Arg Glu Asn Gly Trp Leu Pro Val
        435             440              445
Pro Gly Trp Ser Gly Glu His Glu Trp Arg Gly Trp Ile Pro His Glu
    450             455              460
Ala Met Pro Arg Val Ile Asp Pro Pro Gly Gly Ile Ile Val Thr Ala
465             470              475                      480
Asn Asn Arg Val Val Ala Asp Asp His Pro Asp Tyr Leu Cys Thr Asp
            485             490                          495
Cys His Pro Pro Tyr Arg Ala Glu Arg Ile Met Lys Arg Leu Val Ala
            500             505              510
Asn Pro Ala Phe Ala Val Asp Asp Ala Ala Ala Ile His Ala Asp Thr
        515             520              525
Leu Ser Pro His Val Gly Leu Leu Arg Arg Arg Leu Glu Ala Leu Gly
    530             535              540
Ala Arg Asp Asp Ser Ala Ala Glu Gly Leu Arg Gln Met Leu Val Ala
545             550              555                      560
Trp Asp Gly Arg Met Asp Ala Ala Ser Glu Val Ala Ser Ala Tyr Asn
                565              570                      575
Ala Phe Arg Arg Ala Leu Thr Arg Leu Val Thr Asp Arg Ser Gly Leu
            580             585              590
Glu Gln Ala Ile Ser His Pro Phe Ala Ala Val Ala Pro Gly Val Ser
            595             600              605
Pro Gln Gly Gln Val Trp Trp Ala Val Pro Thr Leu Leu Arg Asp Asp
    610             615              620
Asp Ala Gly Met Leu Lys Gly Trp Ser Trp Asp Gln Ala Leu Ser Glu
625             630              635                      640
Ala Leu Ser Val Ala Ser Gln Asn Leu Thr Gly Arg Ser Trp Gly Glu
                645             650              655
Glu His Arg Pro Arg Phe Thr His Pro Leu Ala Thr Gln Phe Pro Ala
            660             665              670
Trp Ala Gly Leu Leu Asn Pro Ala Ser Arg Pro Ile Gly Gly Asp Gly
            675             680              685
Asp Thr Val Leu Ala Asn Gly Leu Val Pro Ser Ala Gly Pro Gln Ala
690             695              700
```

```
Thr Tyr Gly Ala Leu Ser Arg Tyr Val Phe Asp Val Gly Asn Trp Asp
705             710                 715                 720

Asn Ser Arg Trp Val Val Phe His Gly Ala Ser Gly His Pro Ala Ser
            725             730                 735

Ala His Tyr Ala Asp Gln Asn Ala Pro Trp Ser Asp Cys Ala Met Val
            740             745             750

Pro Met Leu Tyr Ser Trp Asp Arg Ile Ala Ala Glu Ala Val Thr Ser
        755             760             765

Gln Glu Leu Val Pro Ala
        770
```